(12) United States Patent
Benarous et al.

(10) Patent No.: US 12,121,702 B2
(45) Date of Patent: Oct. 22, 2024

(54) DUAL CHAMBER SYRINGE AND METHODS OF USE THEREOF

(71) Applicant: Dali Medical Devices Ltd., Yavne (IL)

(72) Inventors: Nir Benarous, Holon (IL); Ehoud Carmel, Yehud-Monosson (IL); Lior Raday, Kibbutz Bror-Hail (IL); David Daily, Herzliya (IL); Guy Keenan, Tel-Aviv (IL)

(73) Assignee: Dali Medical Devices Ltd, Yavne (IL)

( * ) Notice: Subject to any disclaimer, the term of this patent is extended or adjusted under 35 U.S.C. 154(b) by 0 days.

(21) Appl. No.: 18/460,723

(22) Filed: Sep. 5, 2023

(65) Prior Publication Data

US 2023/0405226 A1    Dec. 21, 2023

Related U.S. Application Data

(62) Division of application No. 16/994,596, filed on Aug. 16, 2020, now Pat. No. 11,779,705.

(60) Provisional application No. 62/911,383, filed on Oct. 7, 2019.

(51) Int. Cl.
*A61M 5/19* (2006.01)
*A61M 5/31* (2006.01)
*A61M 5/315* (2006.01)

(52) U.S. Cl.
CPC ............ *A61M 5/19* (2013.01); *A61M 5/3137* (2013.01); *A61M 5/31511* (2013.01); *A61M 5/31515* (2013.01); *A61M 5/31581* (2013.01)

(58) Field of Classification Search
CPC .......... A61M 5/31596; A61M 5/31581; A61M 5/31515; A61M 5/31511; A61M 5/3137; A61M 5/284; A61M 5/2448; A61M 5/2066; A61M 5/19; A61M 2005/3139; A61M 2005/3132
See application file for complete search history.

(56) References Cited

U.S. PATENT DOCUMENTS

| | | | |
|---|---|---|---|
| 4,874,381 A | 10/1989 | Vetter | |
| 5,496,285 A * | 3/1996 | Schumacher | ..... A61M 5/31513 604/218 |
| 8,517,983 B2 | 8/2013 | Kakiuchi et al. | |
| 10,765,811 B2 | 9/2020 | Vedrine | |

(Continued)

FOREIGN PATENT DOCUMENTS

| | | |
|---|---|---|
| EP | 2 641 628 A1 | 9/2013 |
| WO | 2012067141 A1 | 5/2012 |

*Primary Examiner* — James D Ponton
*Assistant Examiner* — Hong-Van N Trinh
(74) *Attorney, Agent, or Firm* — Naomi S. Rosenman-Helfand

(57) ABSTRACT

A dual chamber syringe, comprising a syringe barrel having a forward end, a rearward end and at least one bypass protrusion arranged along the longitudinal extent of the syringe barrel; a finger grip element coupled to the rearward end of the syringe barrel, the finger grip comprises at least one protrusion extending radially inwardly from an inner surface thereof; a plunger rod operatively coupled with the finger grip element; a guiding track is formed on the plunger rod and comprises a helical track portion and a longitudinal track portion; and wherein upon relative displacement of the plunger rod and said finger grip element, the at least one protrusion is guided along the guiding track.

11 Claims, 35 Drawing Sheets

(56) References Cited

U.S. PATENT DOCUMENTS

2012/0095394 A1* 4/2012 Kakiuchi .............. A61M 5/284
 604/89
2014/0005610 A1* 1/2014 Kakiuchi .......... A61M 5/31586
 604/227
2014/0058320 A1 2/2014 Hansen

* cited by examiner

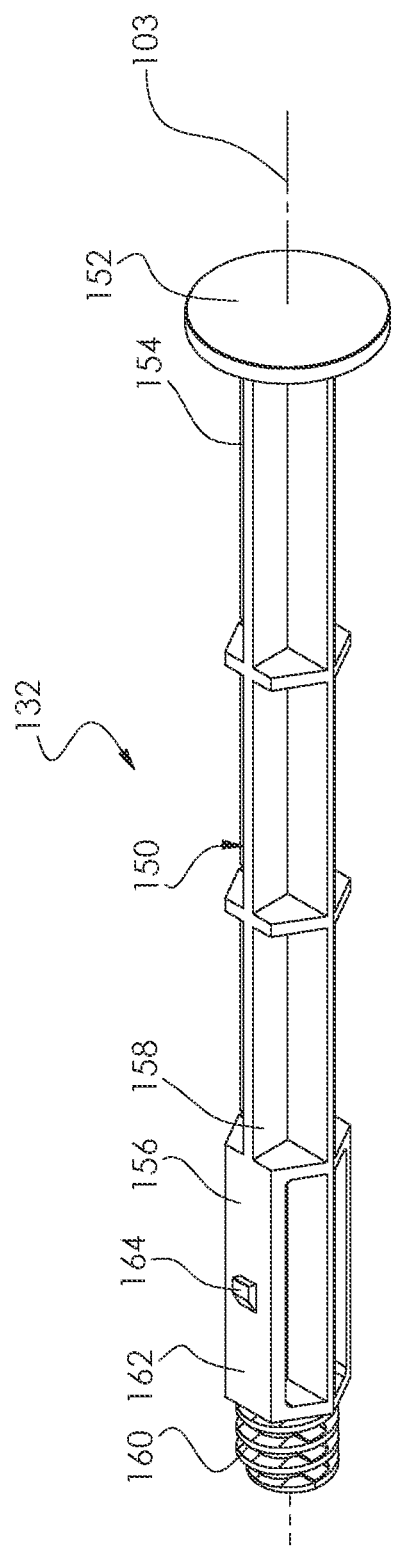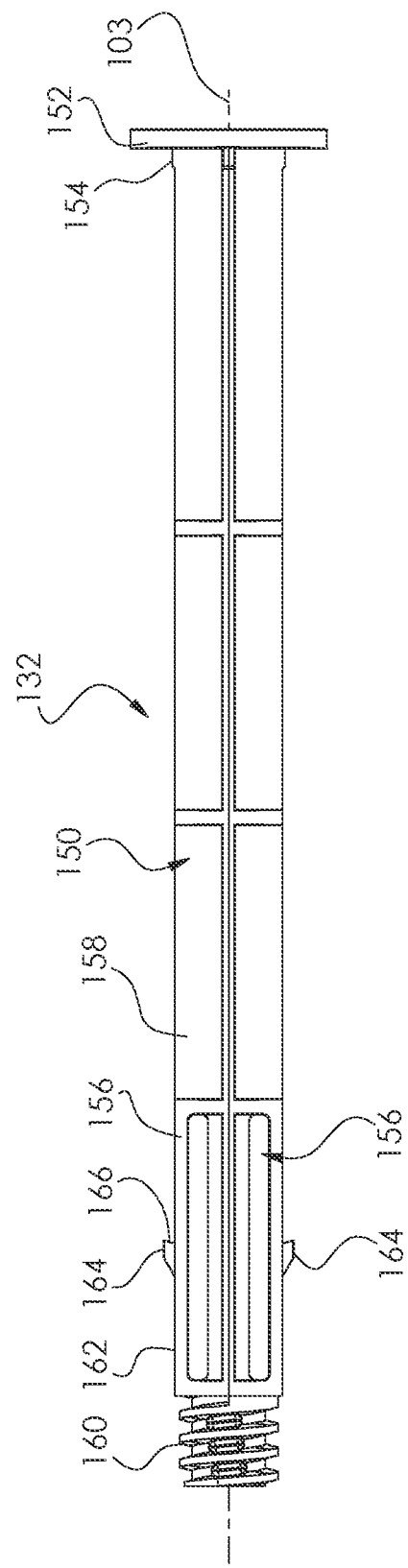
Fig. 2A
Fig. 2B

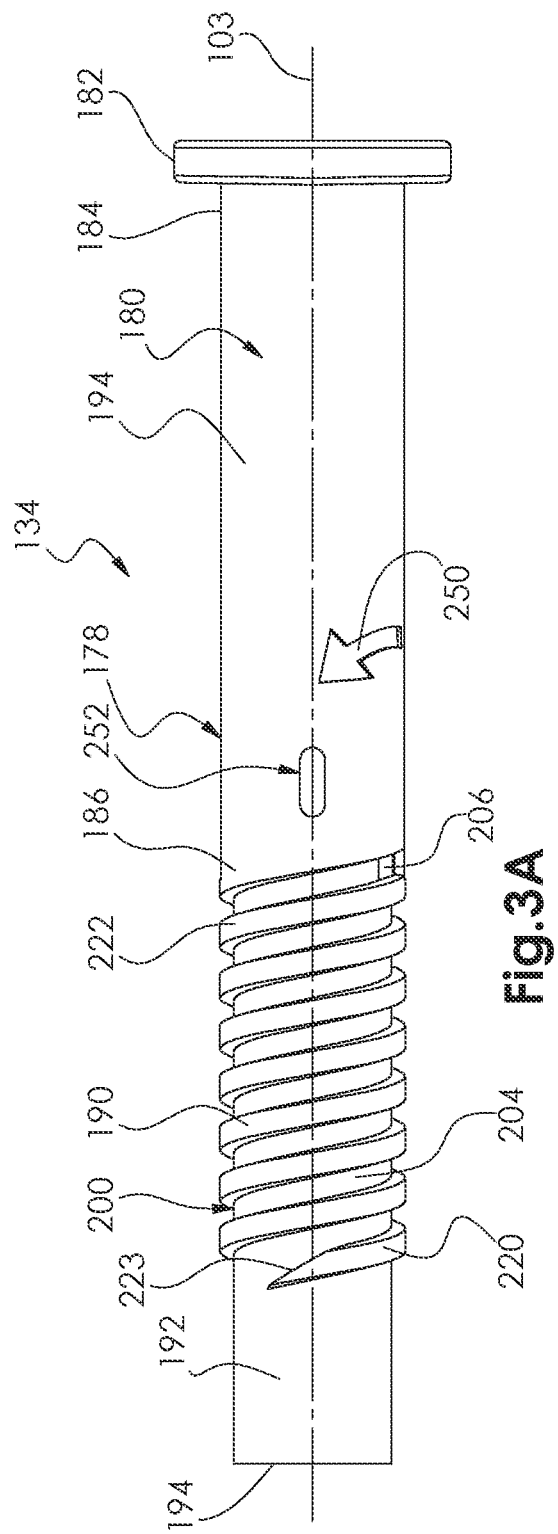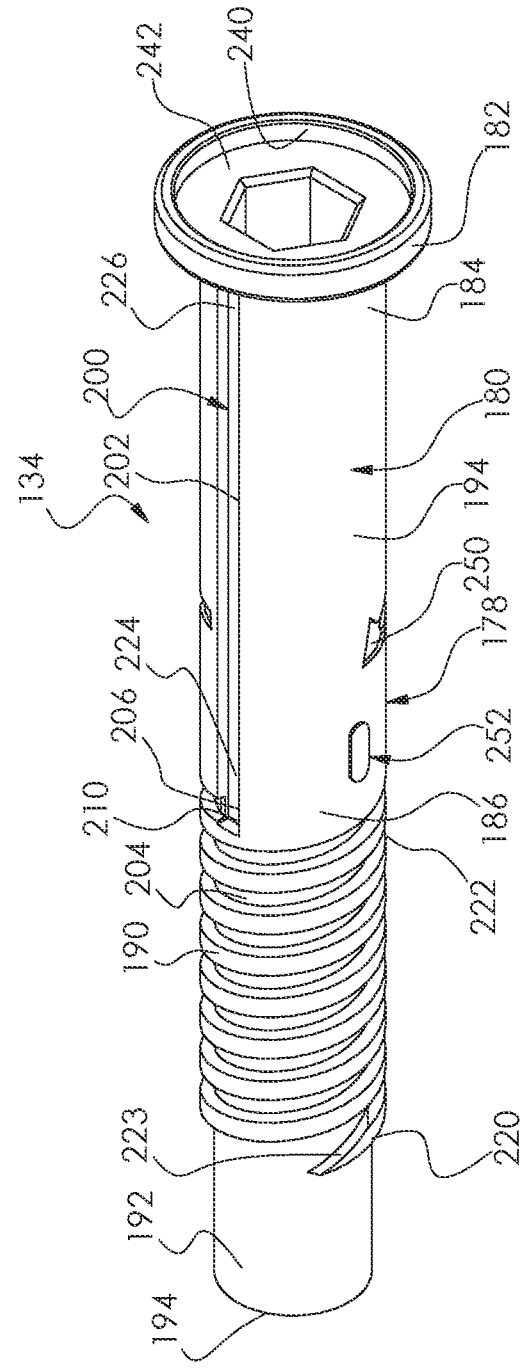

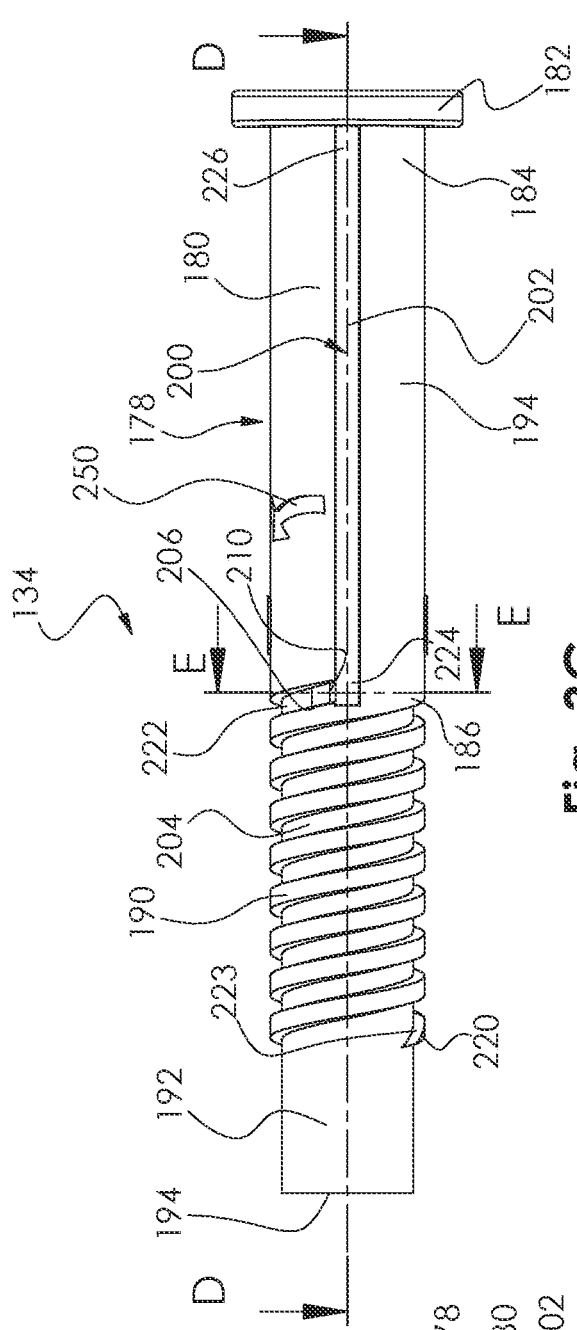
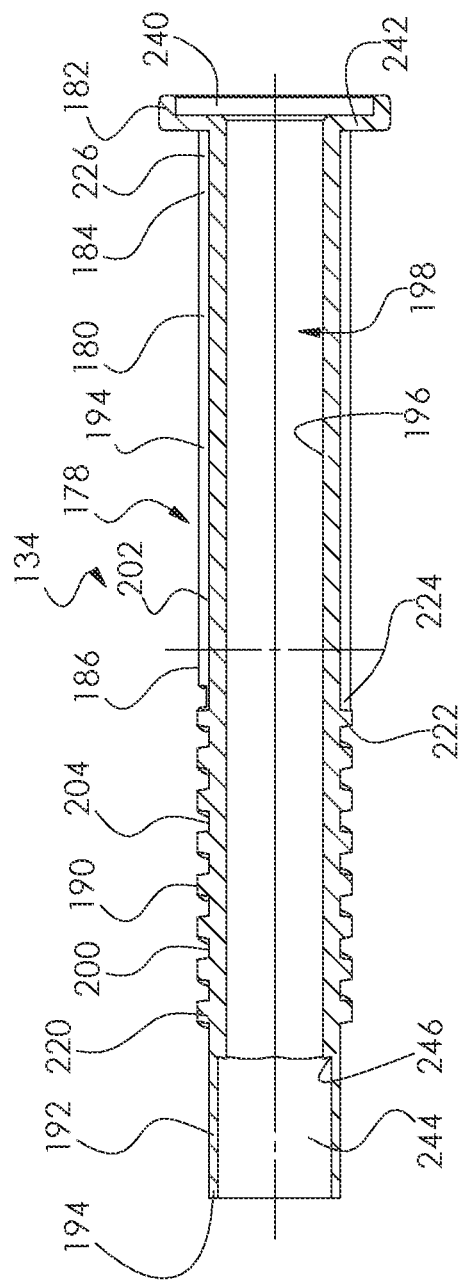
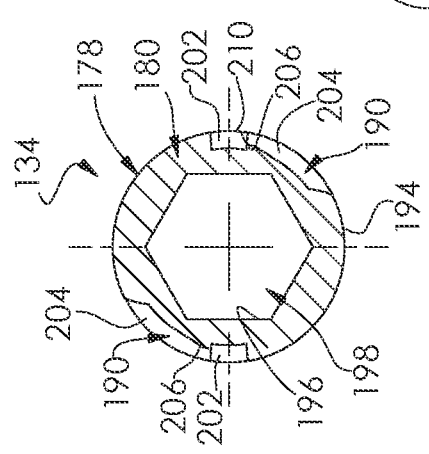
Fig. 3C
Fig. 3D
Fig. 3E

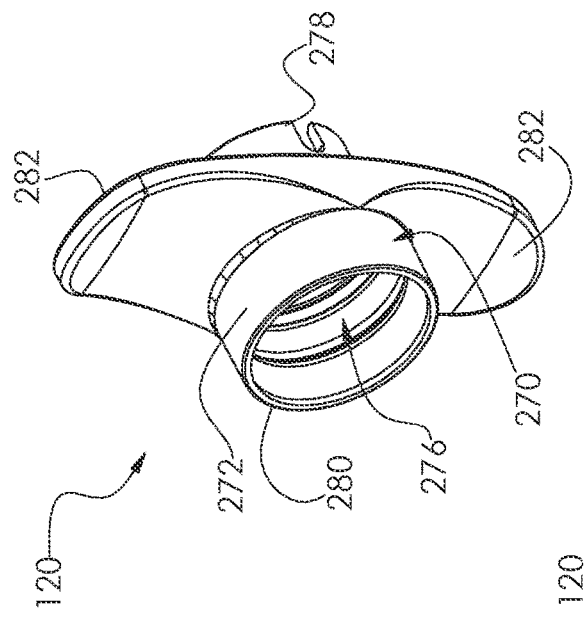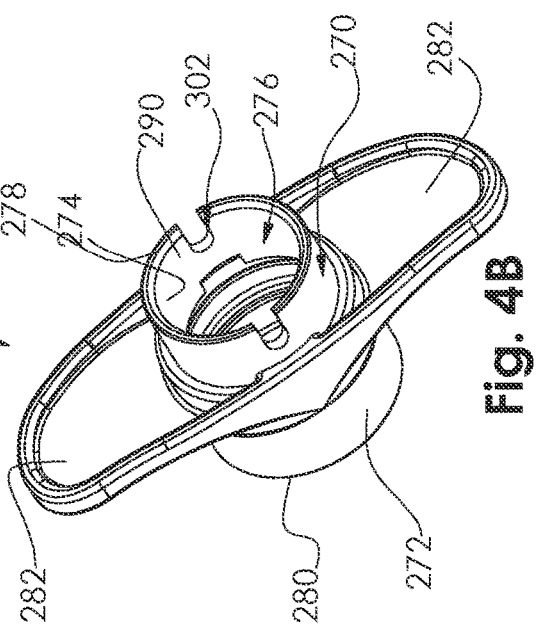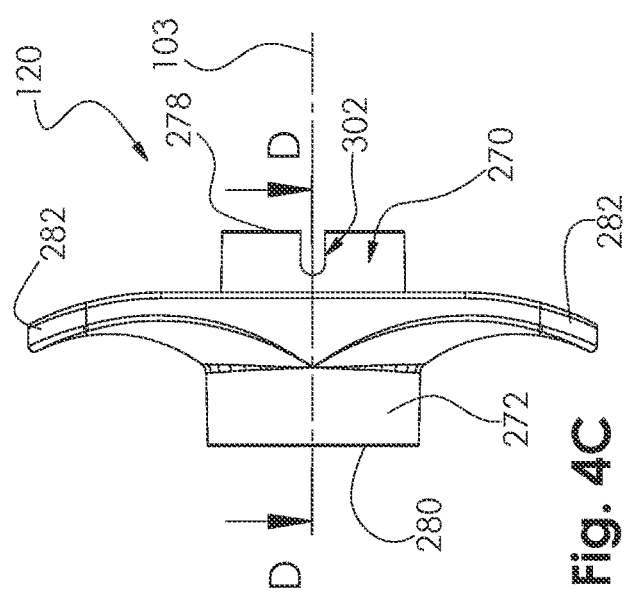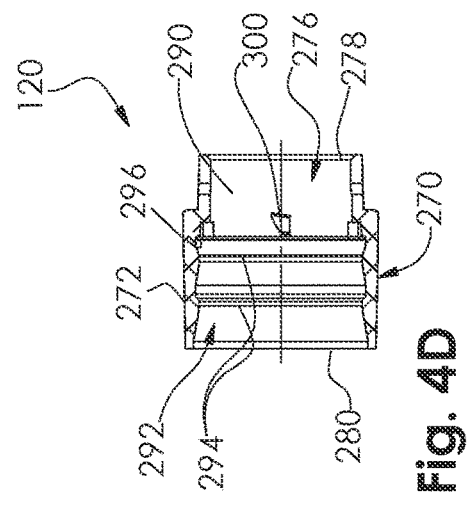

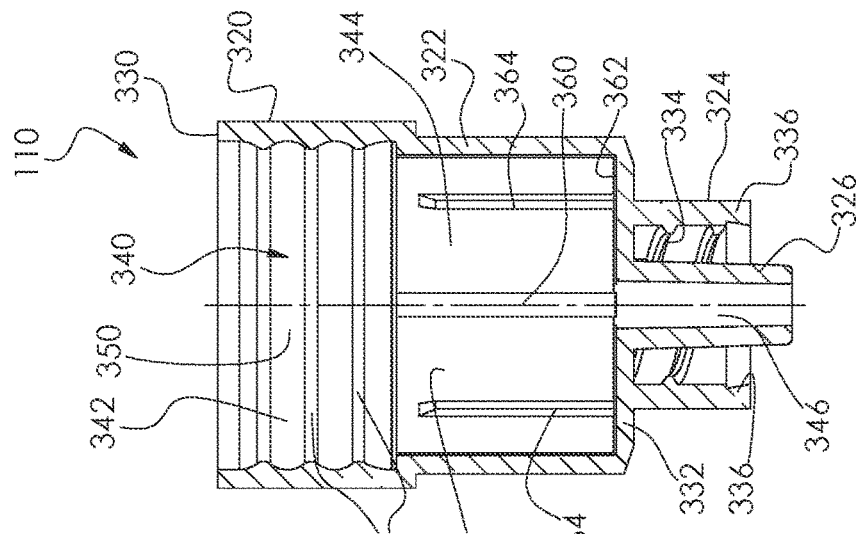
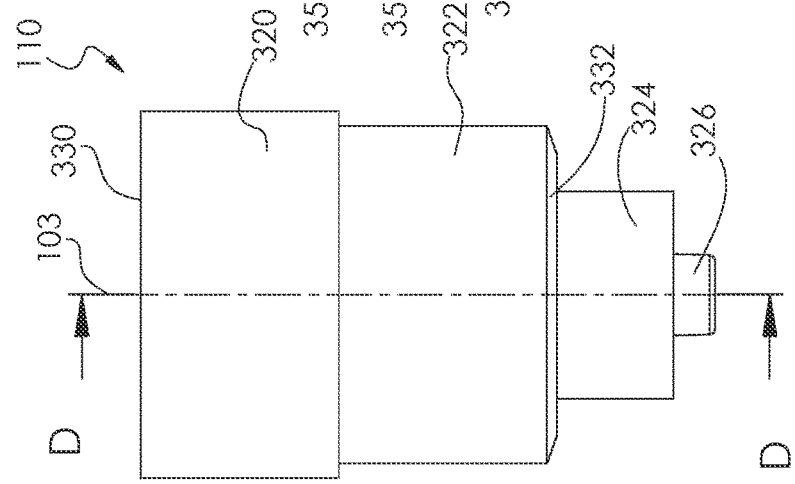
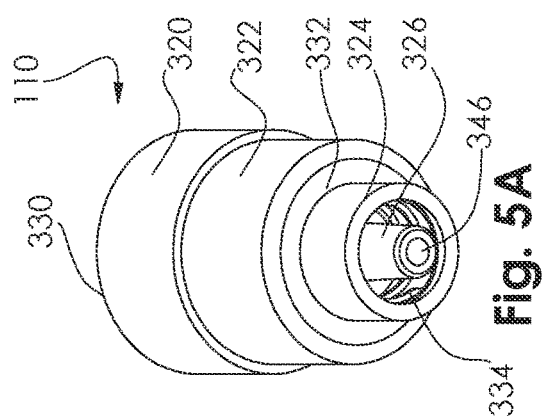
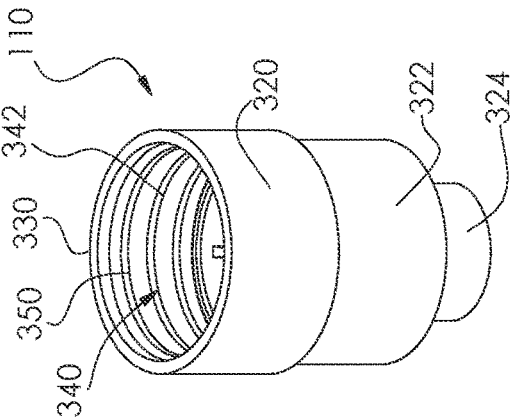

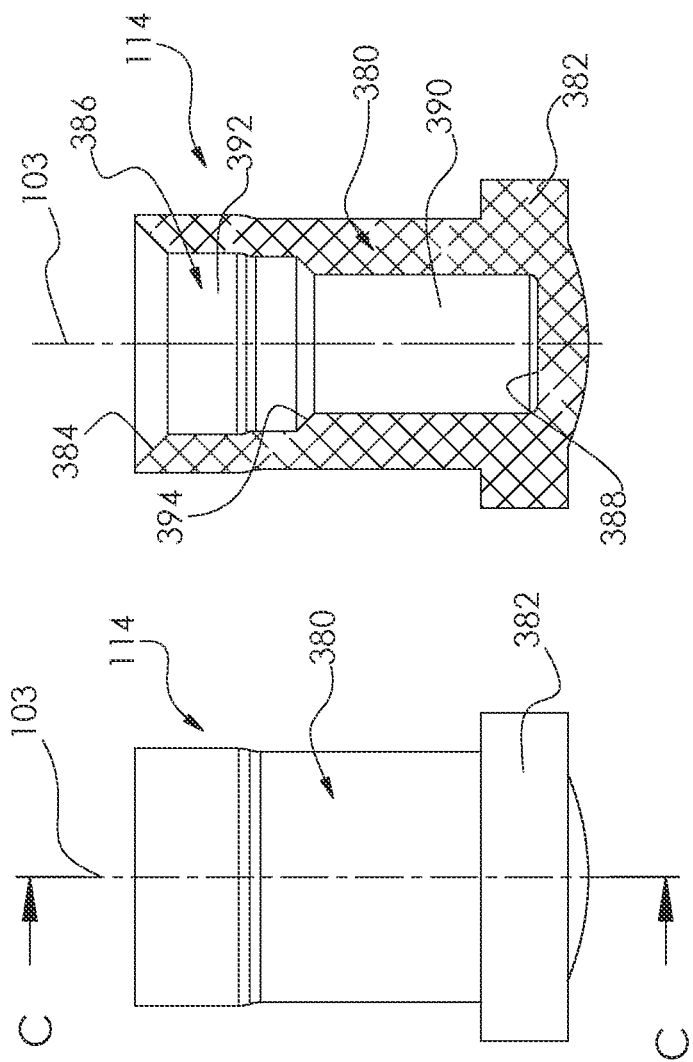
Fig. 6C
Fig. 6B
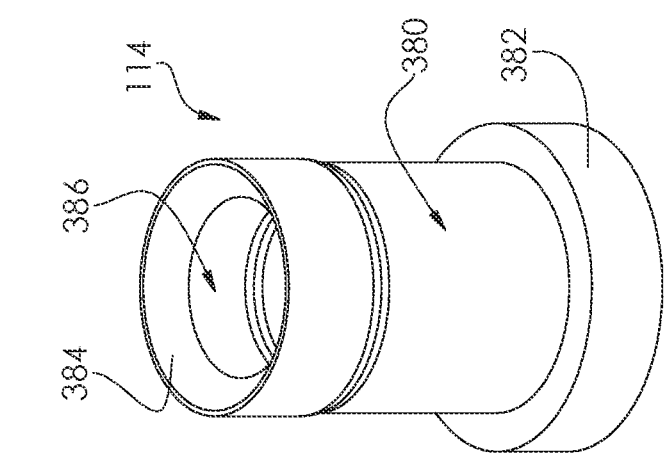
Fig. 6A

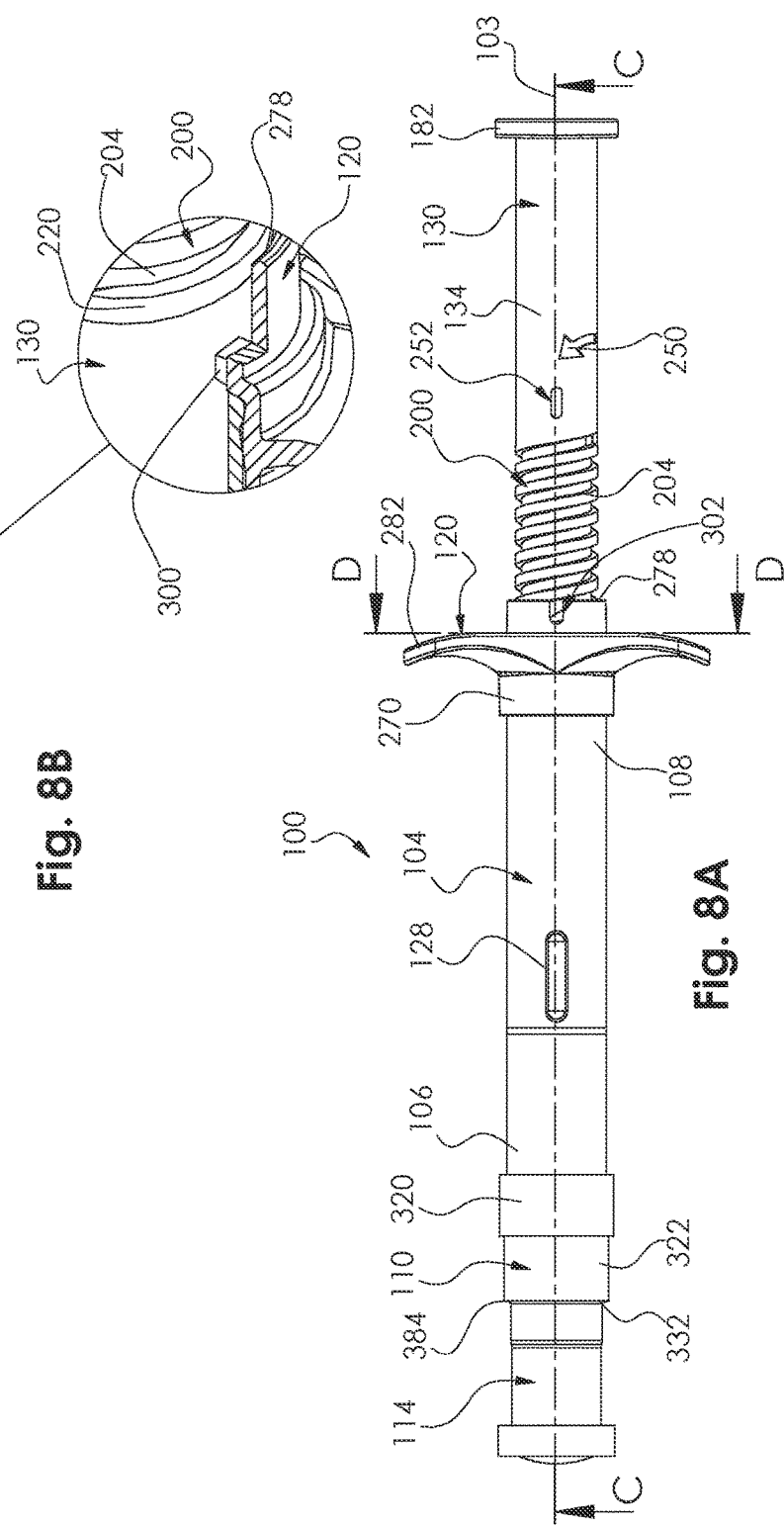
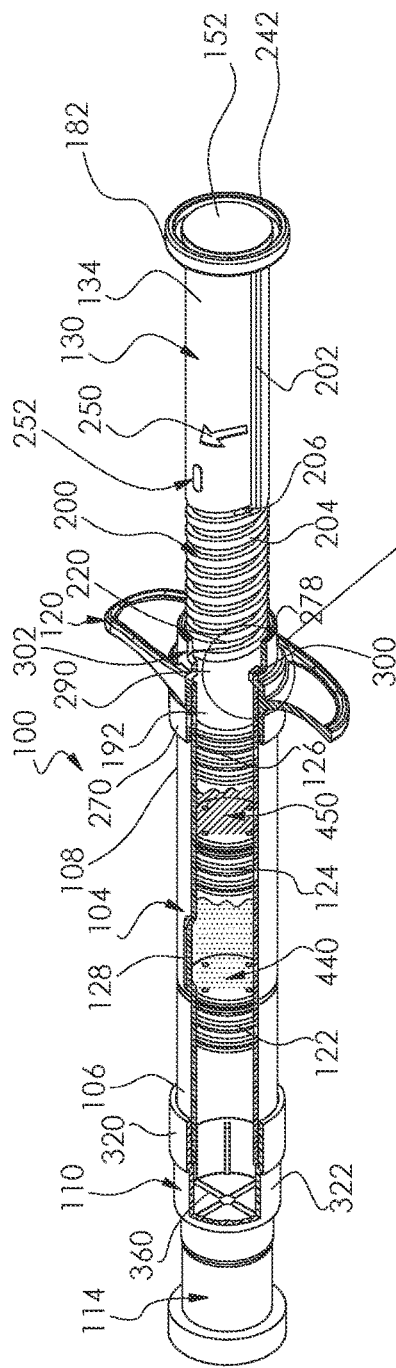
Fig. 8A
Fig. 8B

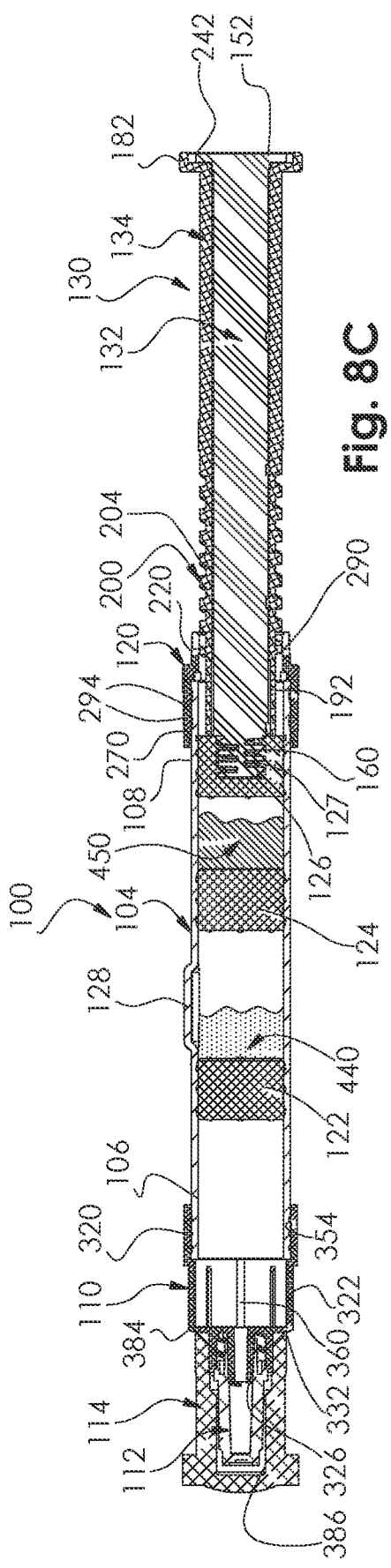
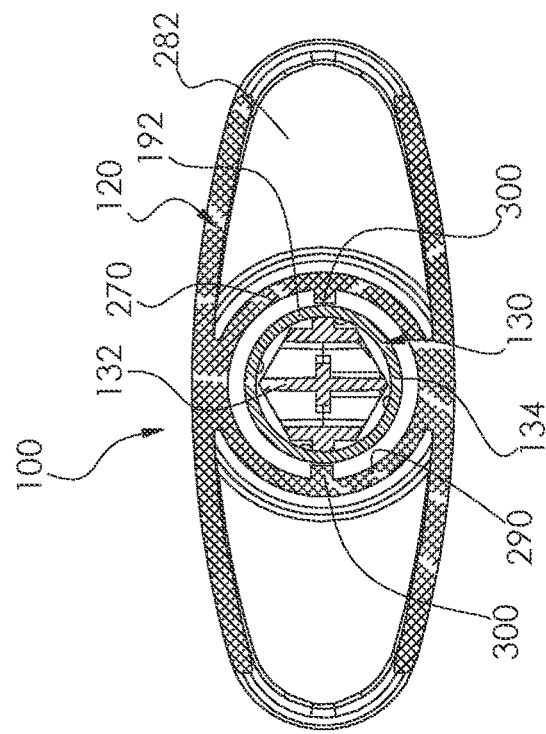
Fig. 8C
Fig. 8D

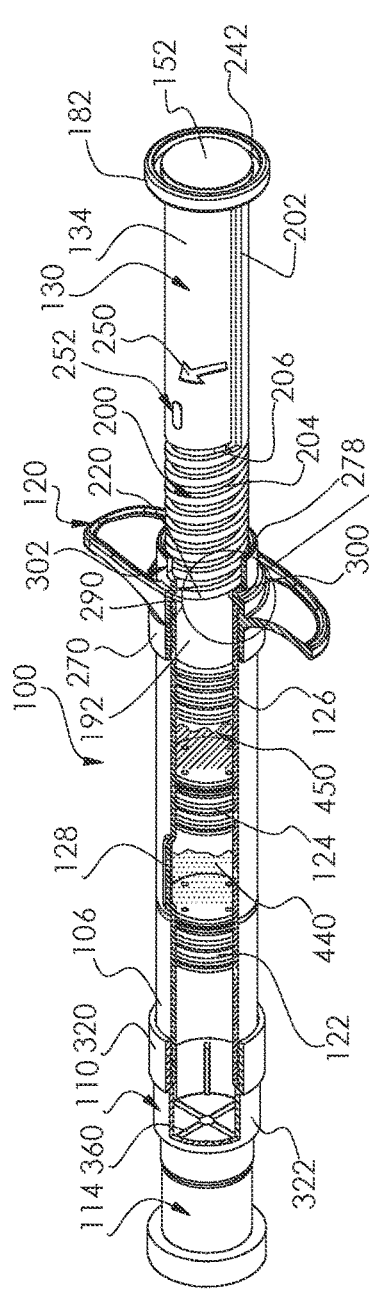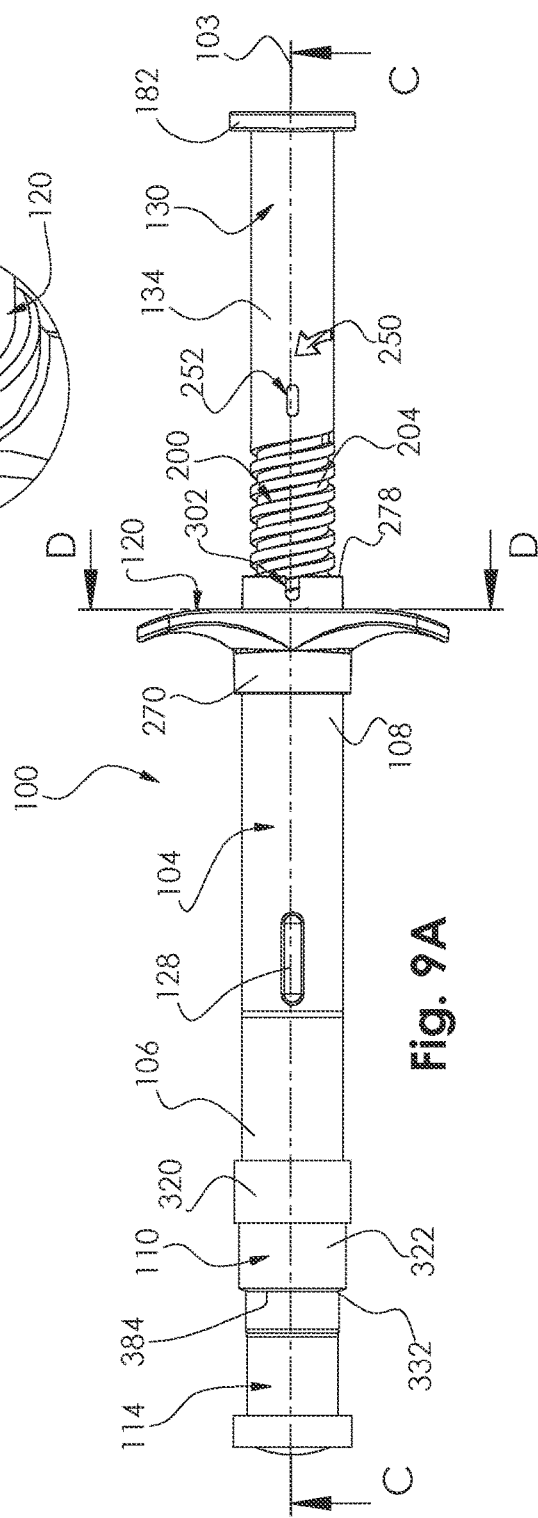

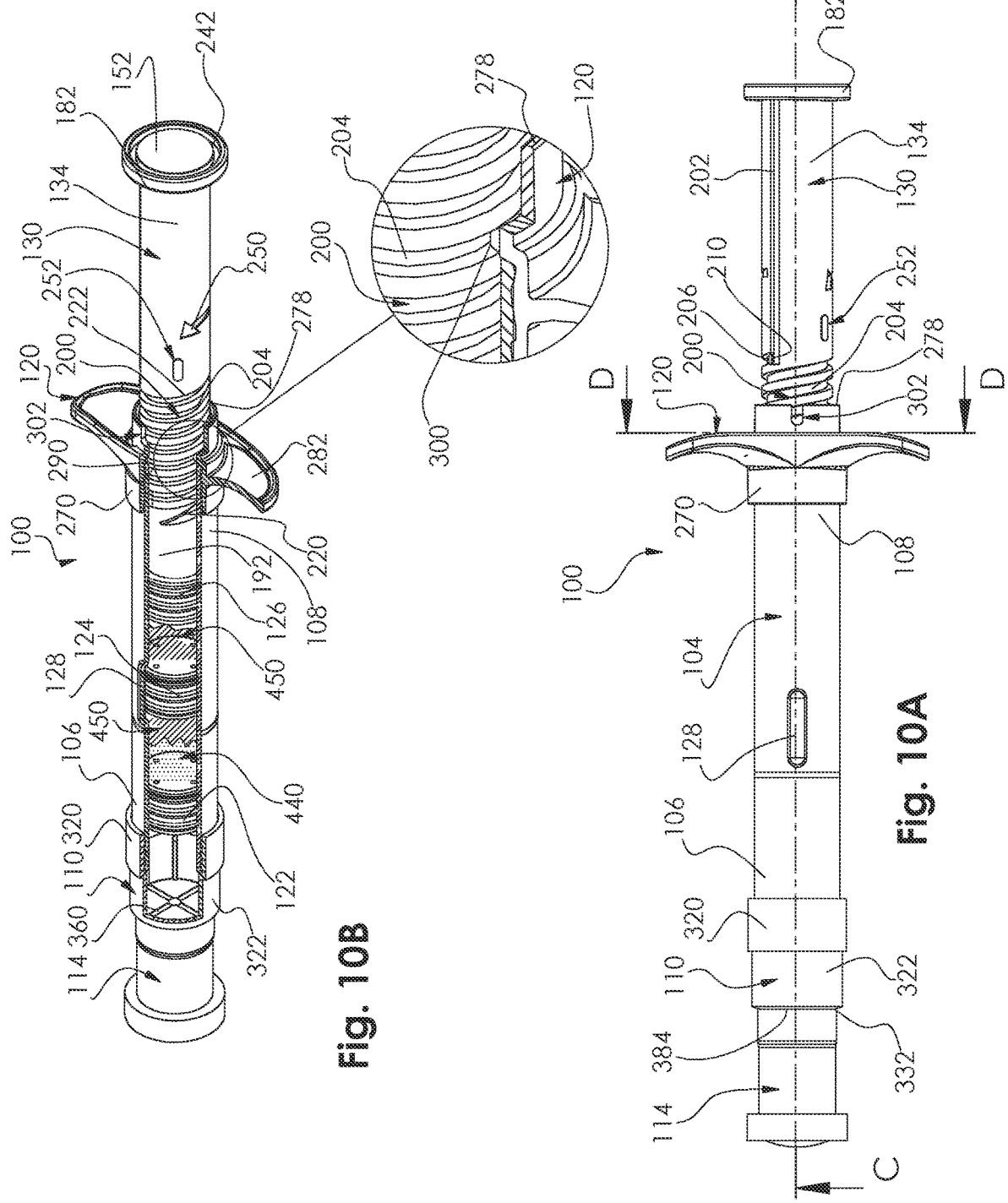

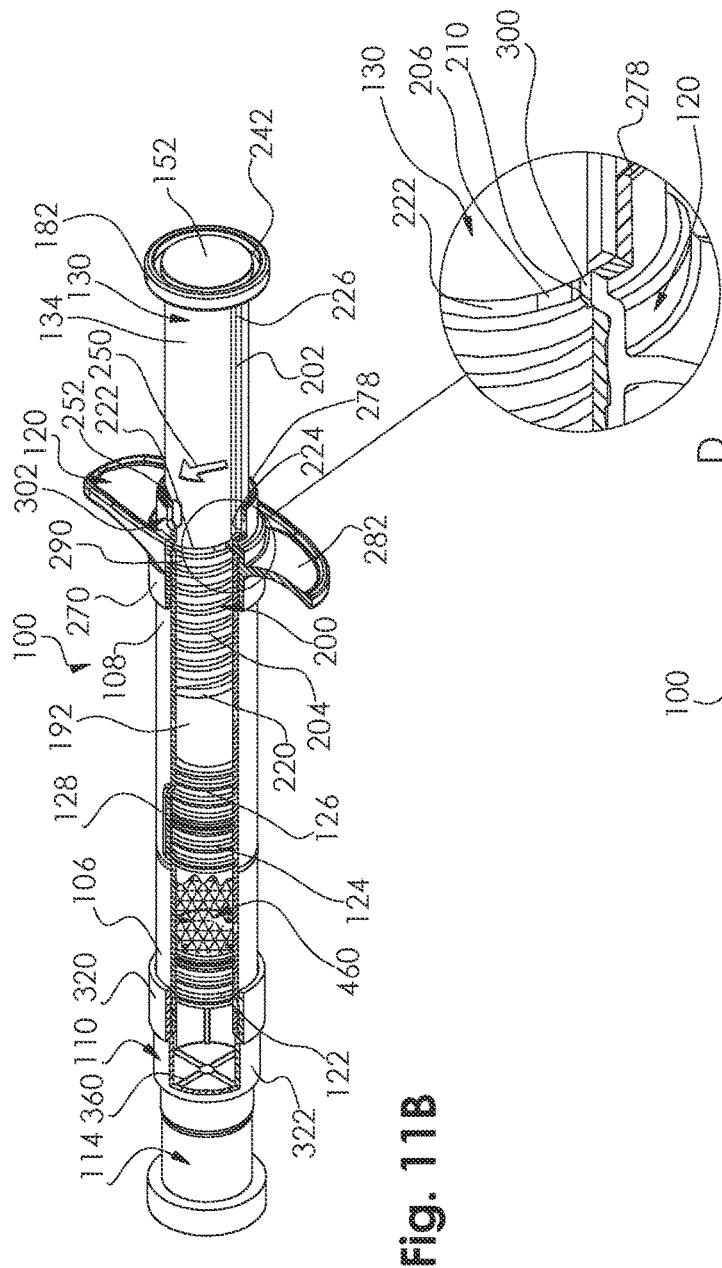
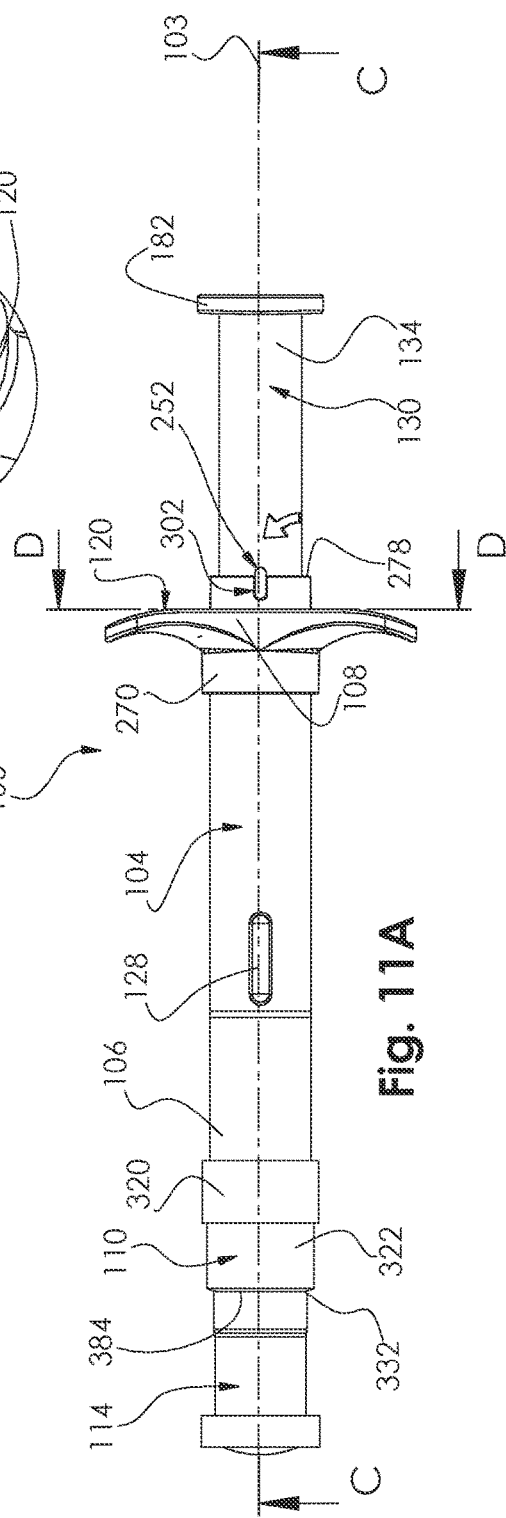
Fig. 11B
Fig. 11A

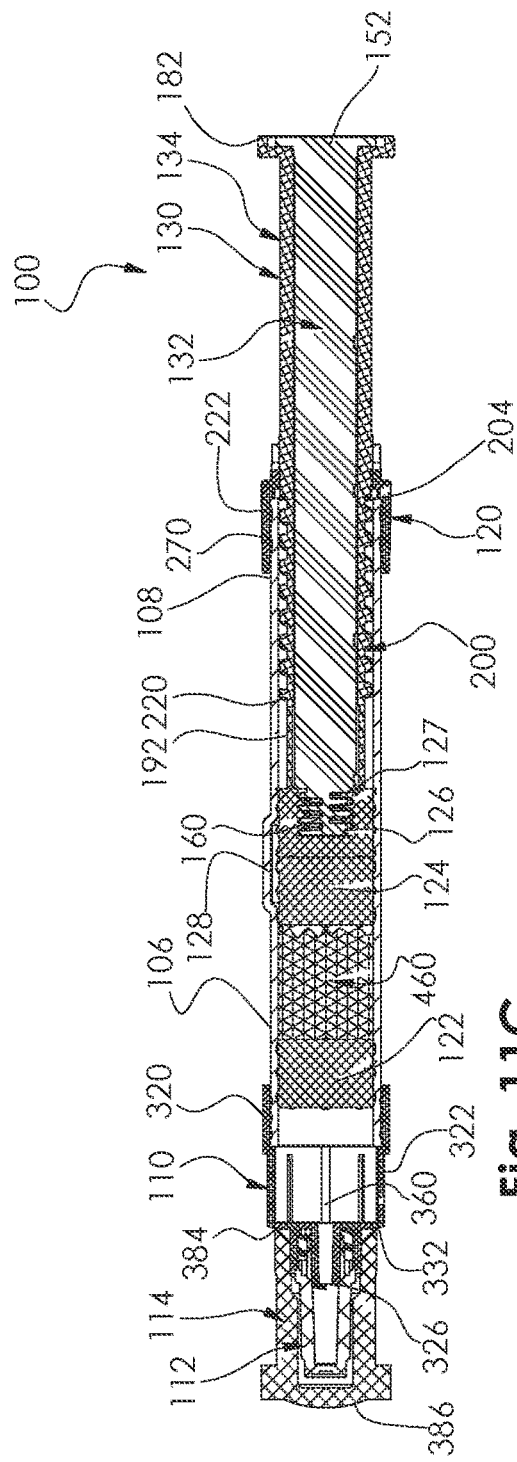
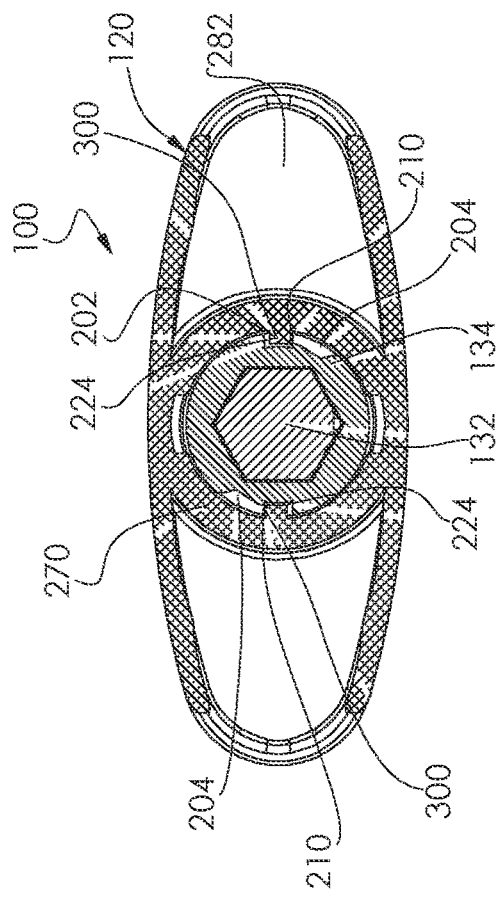
Fig. 11C
Fig. 11D

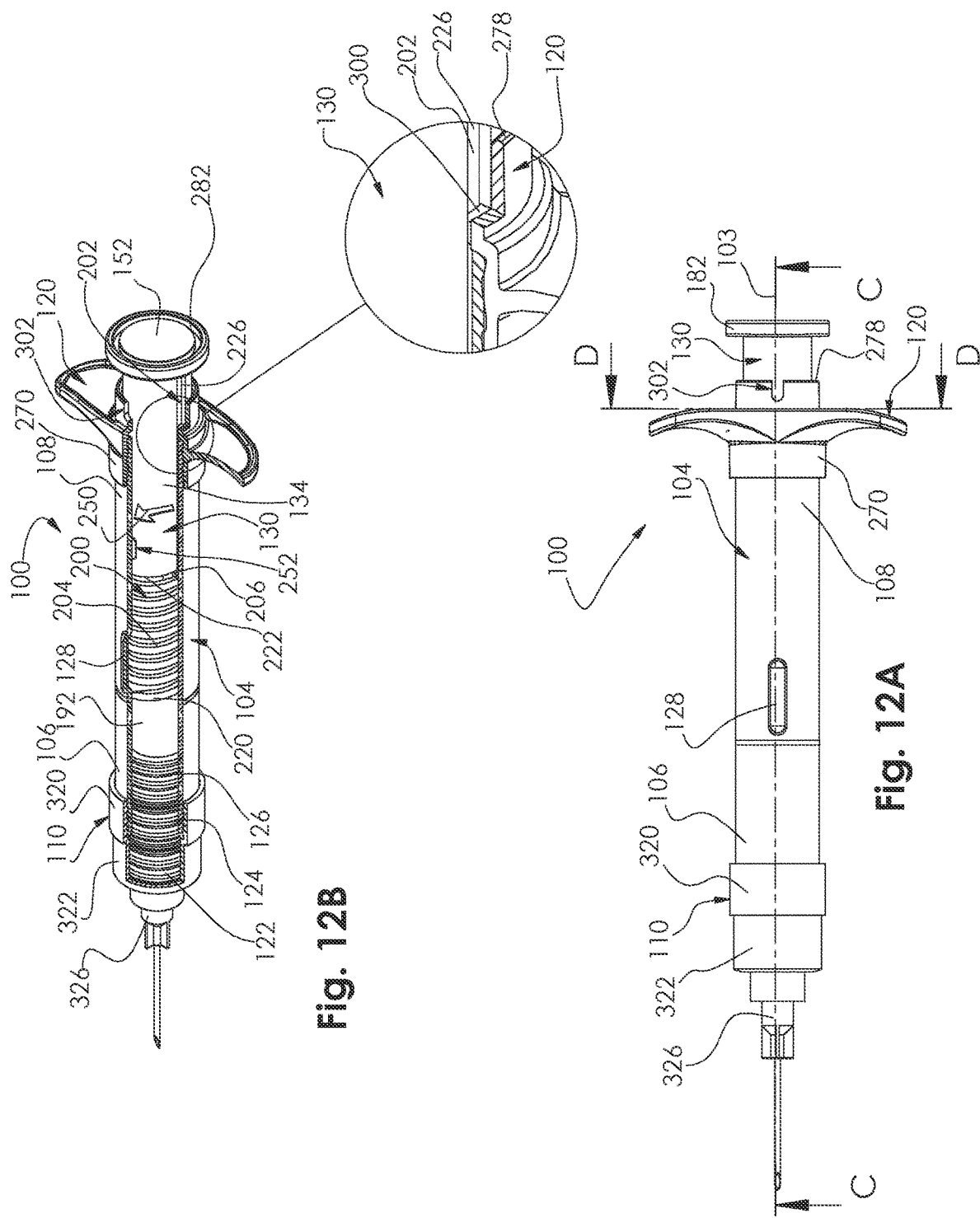

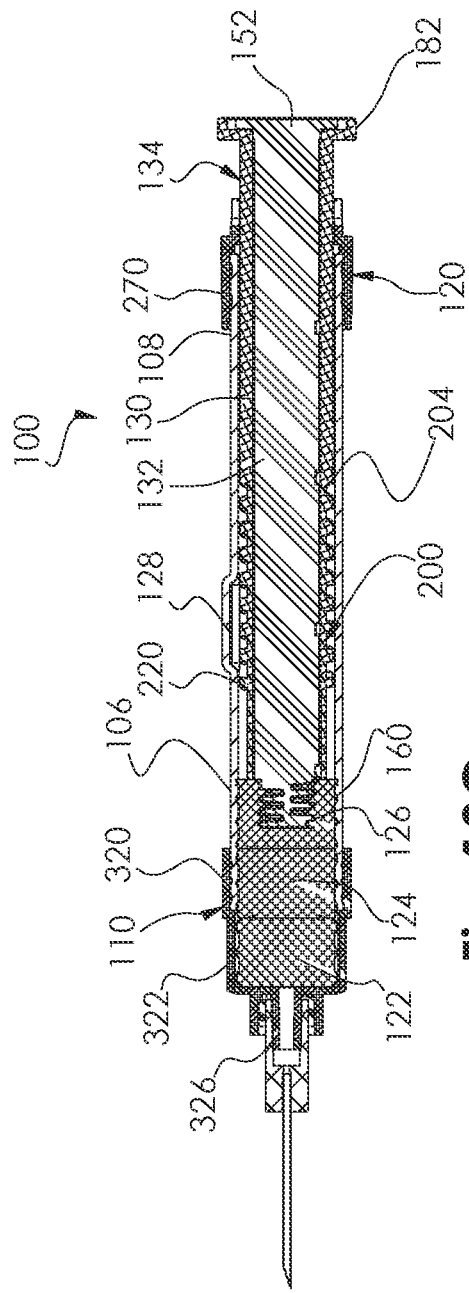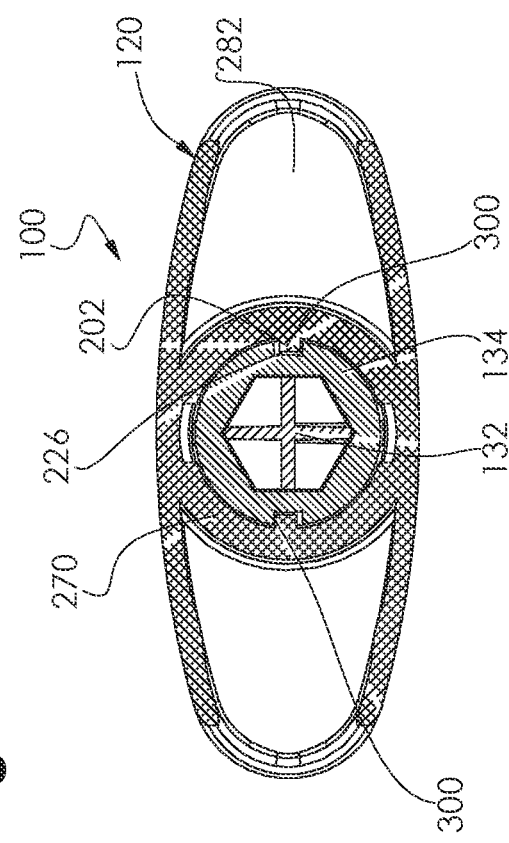

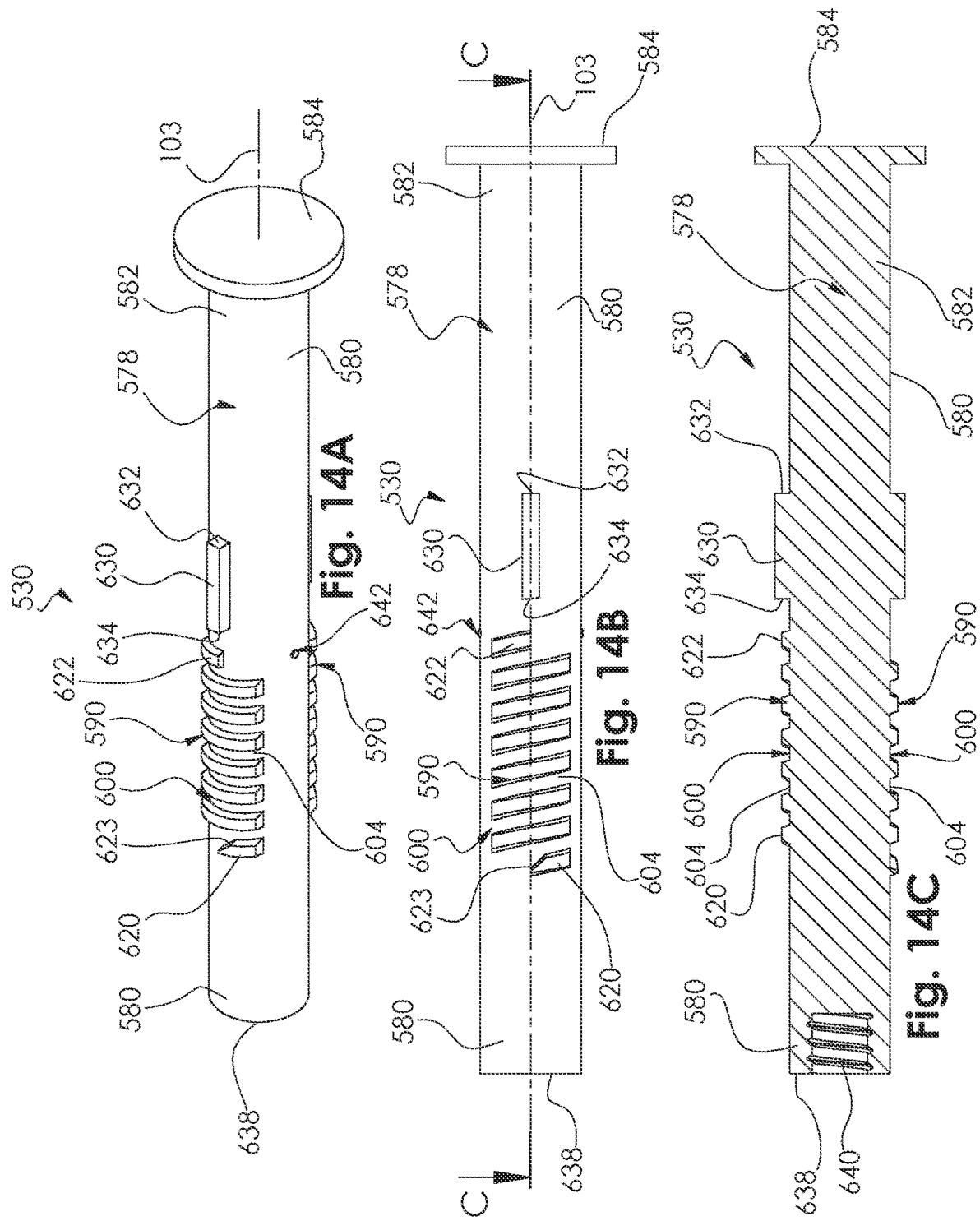

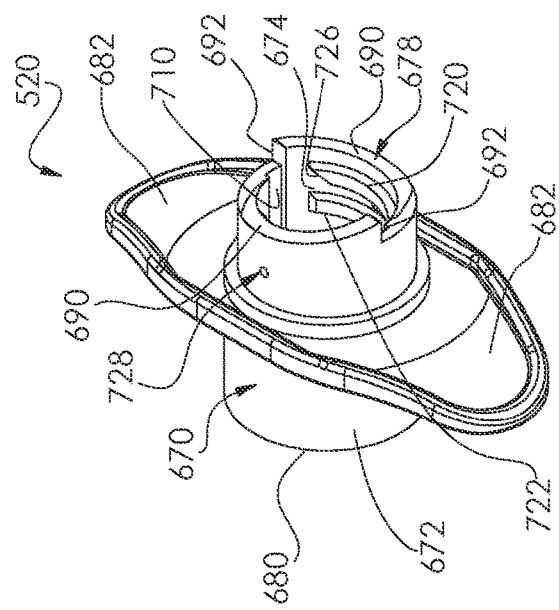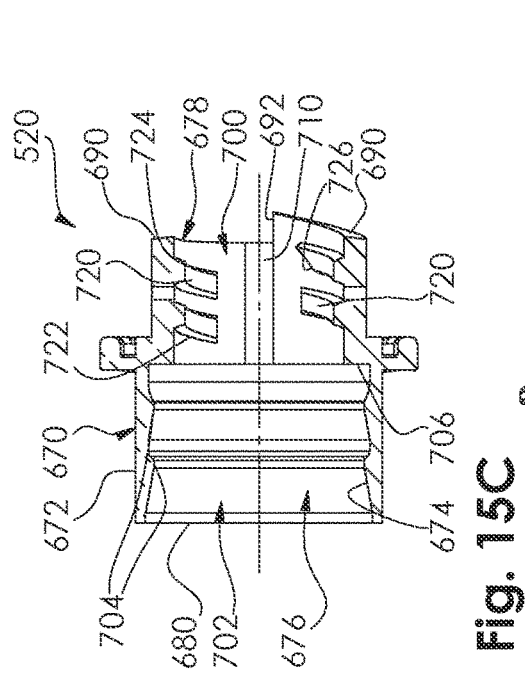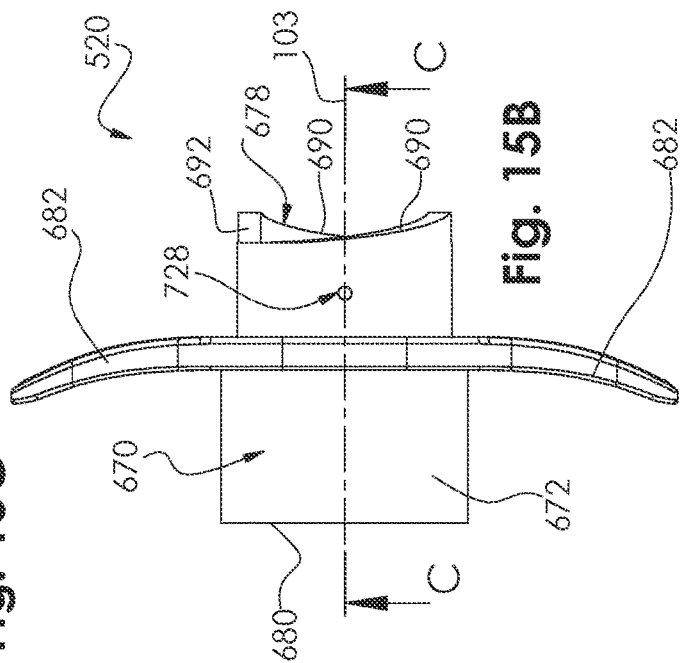

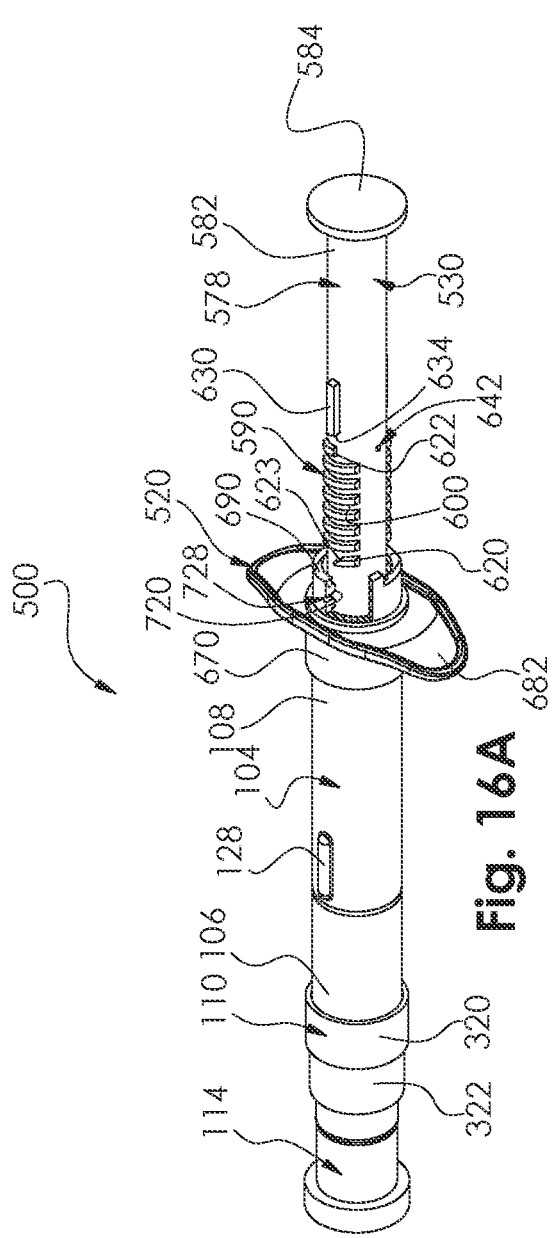
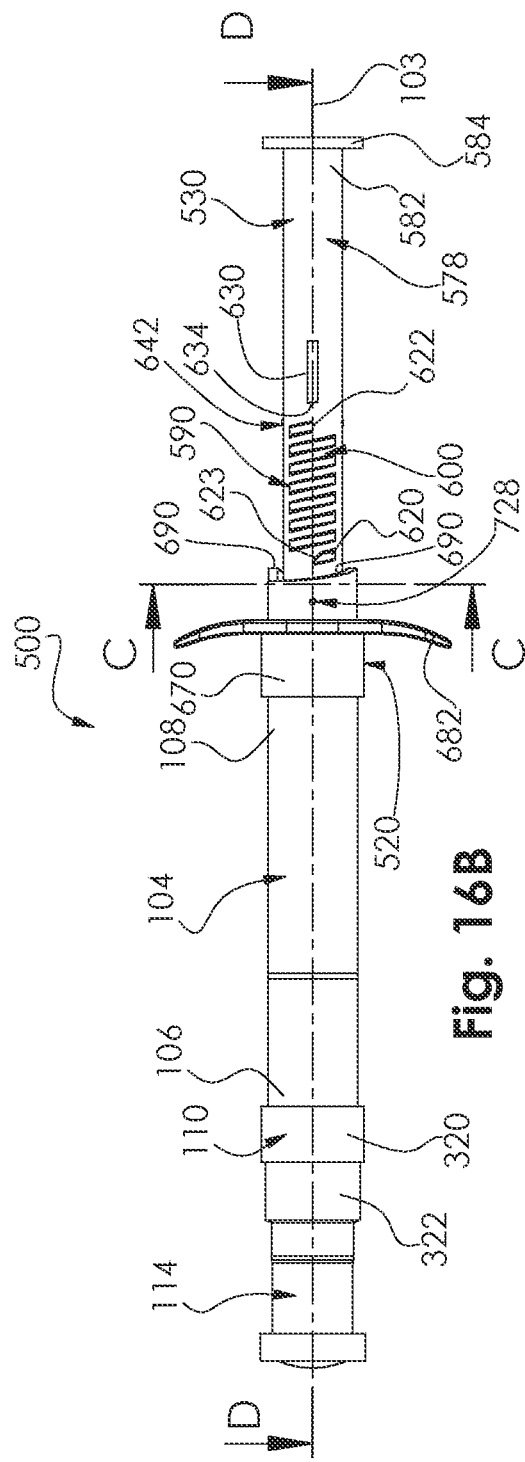
Fig. 16A
Fig. 16B

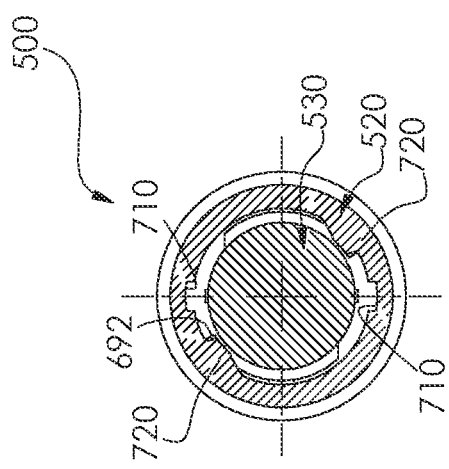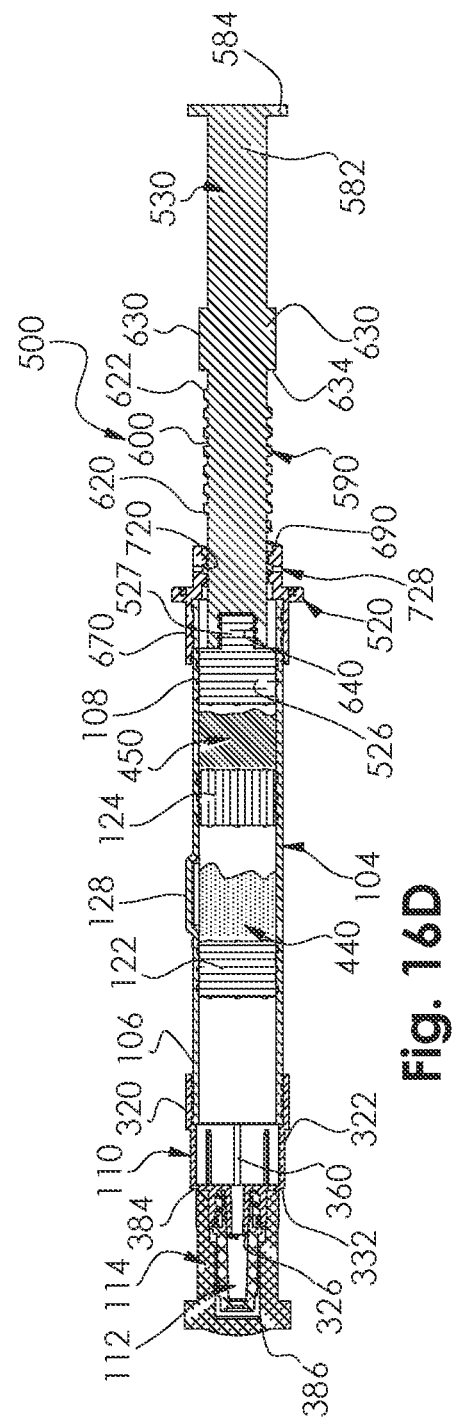

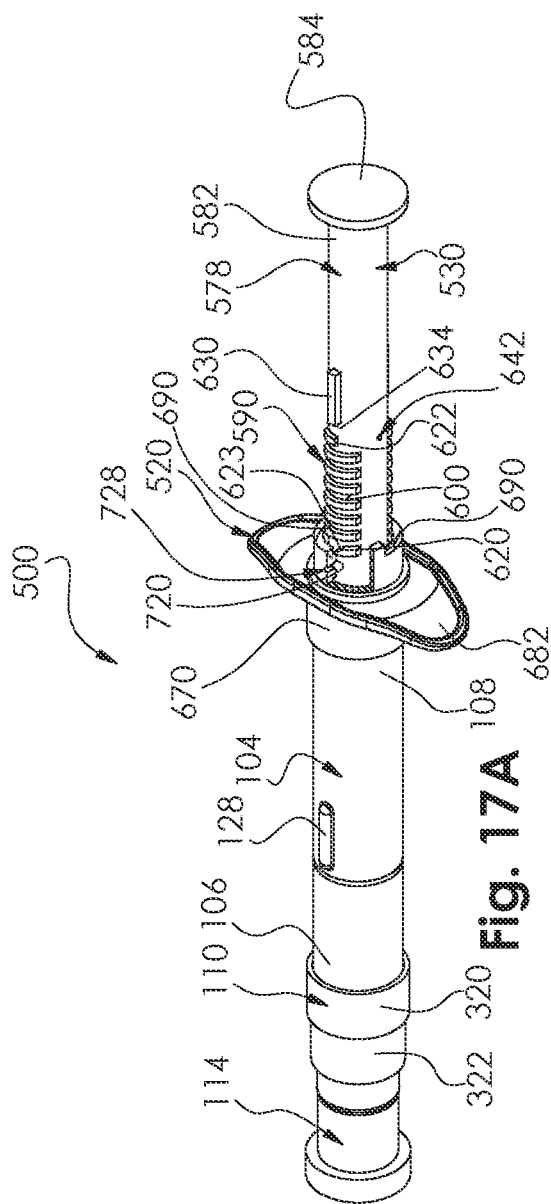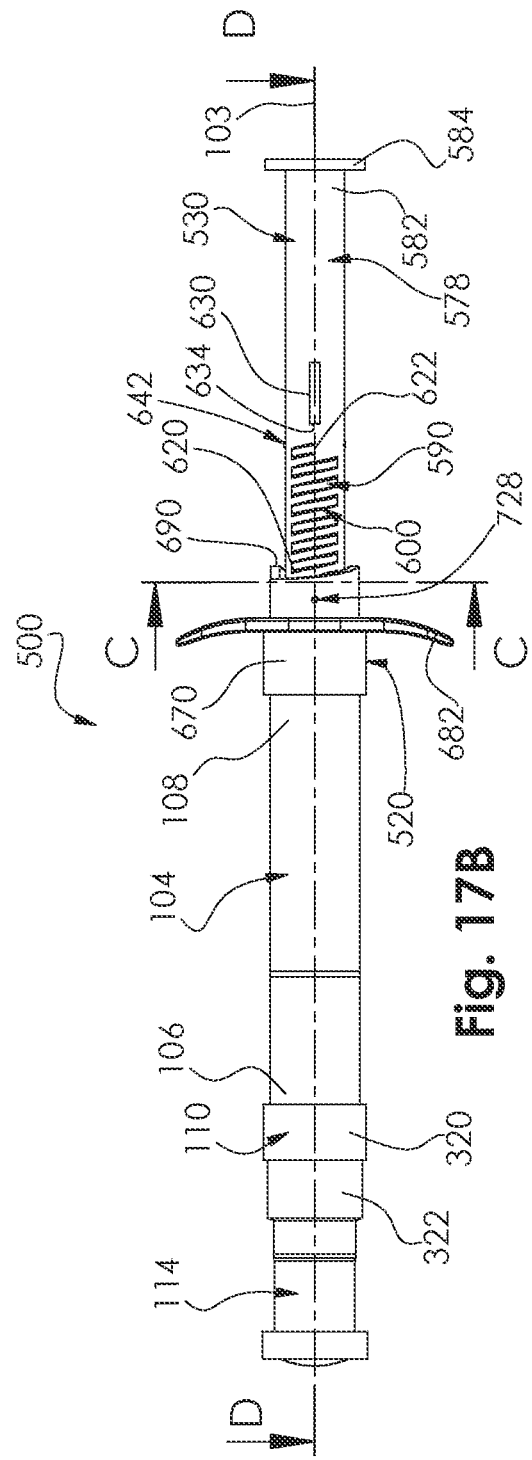

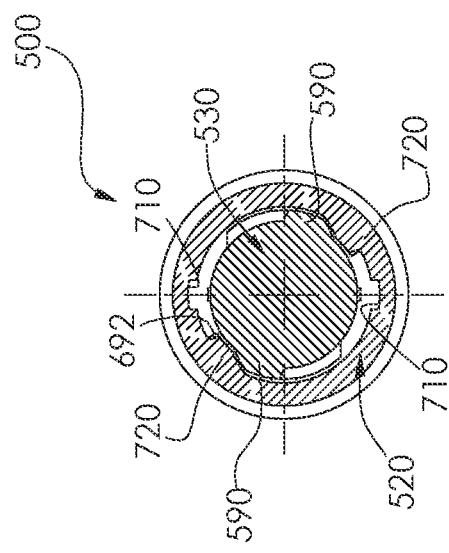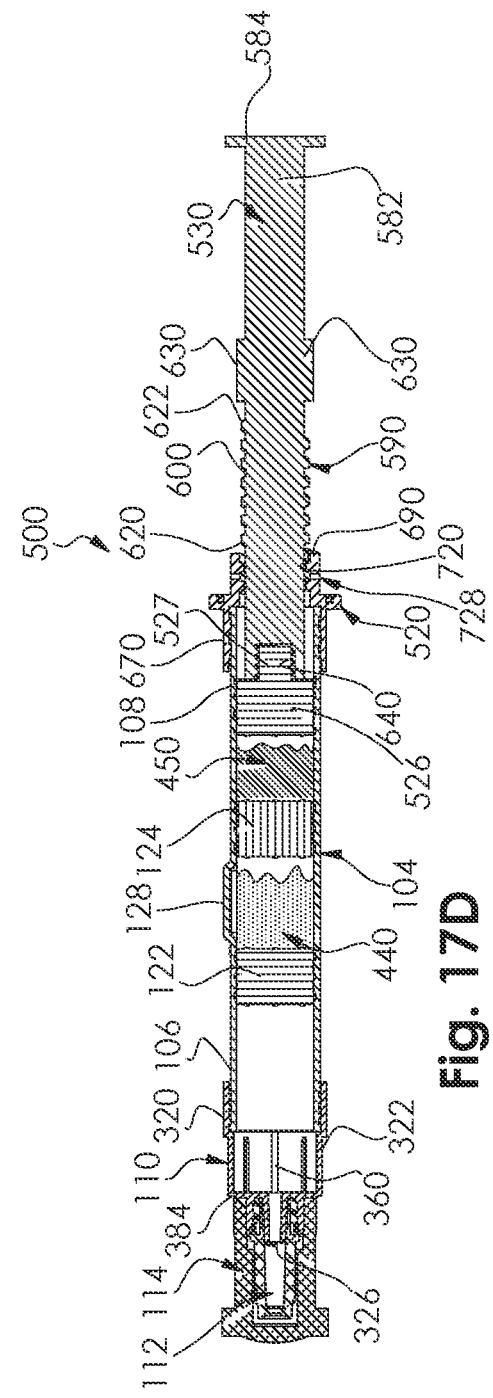

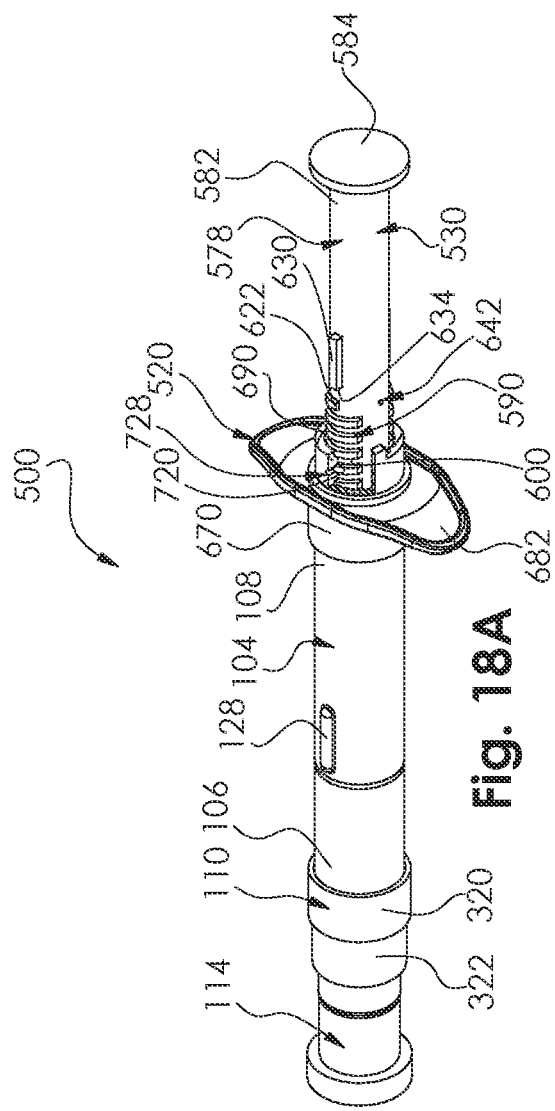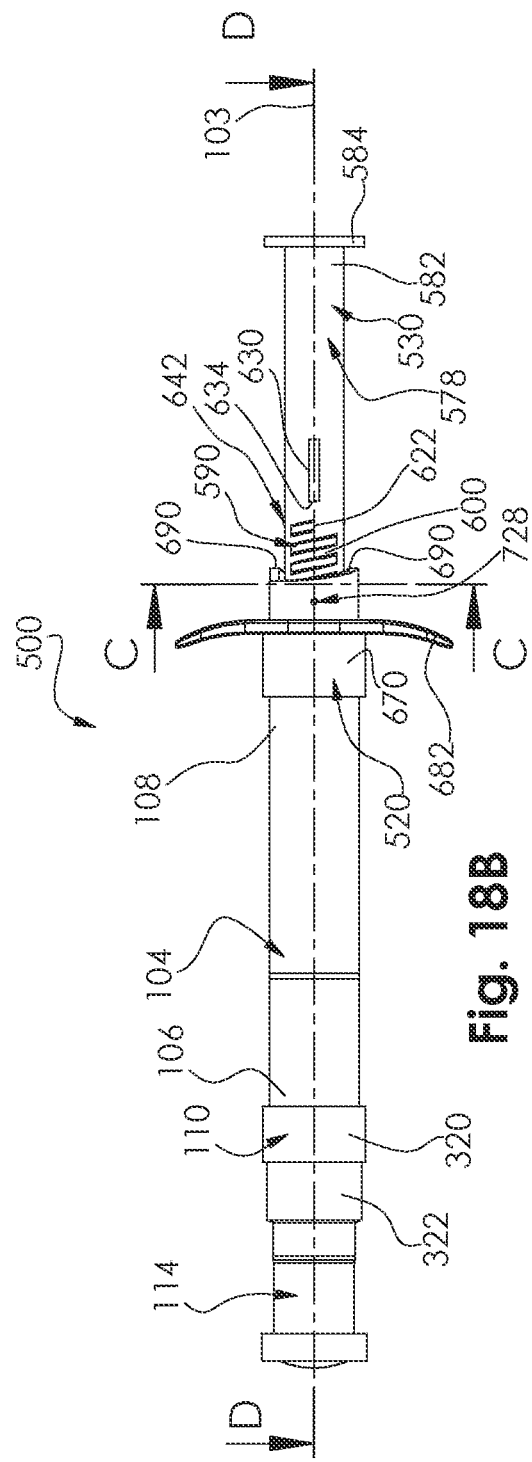

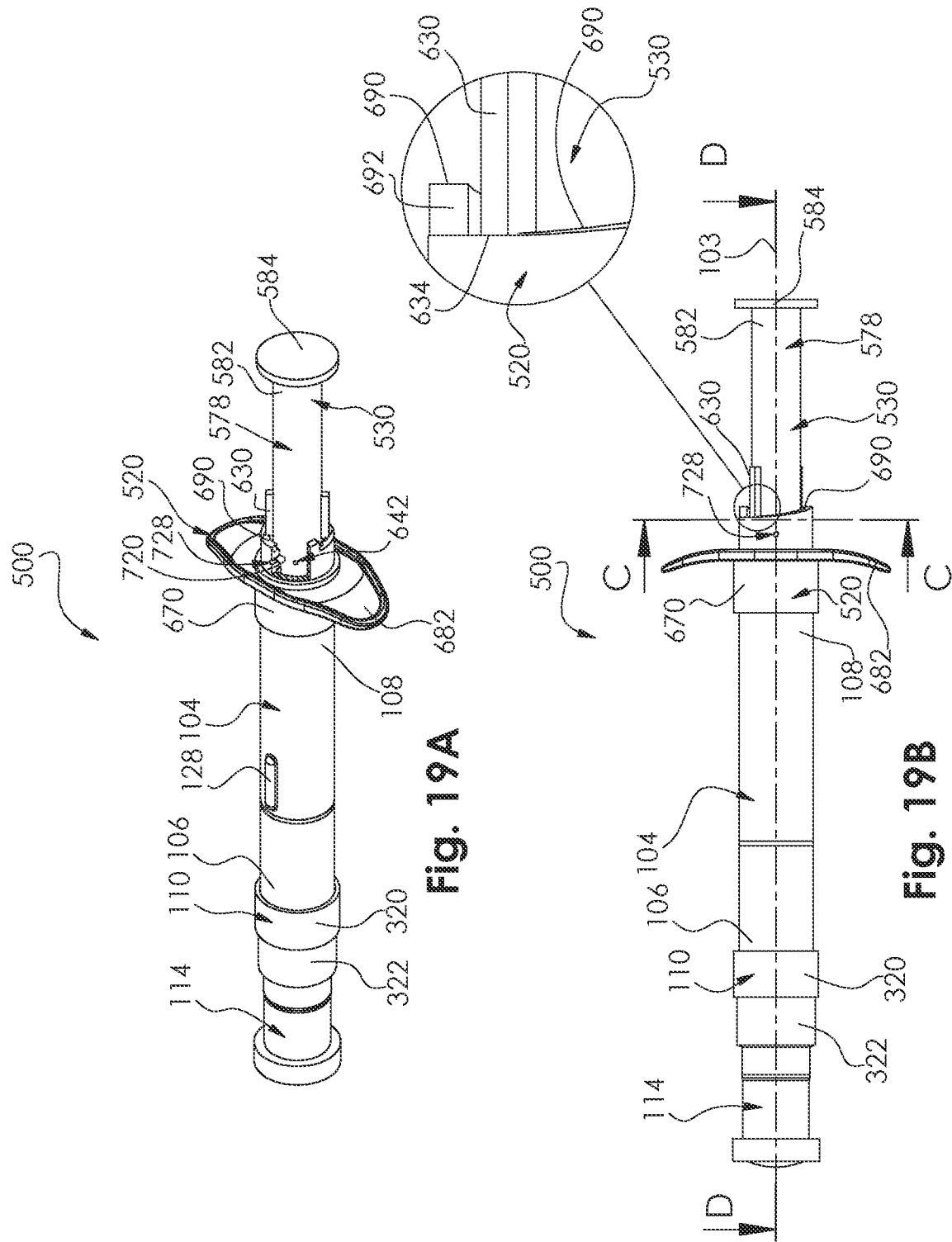

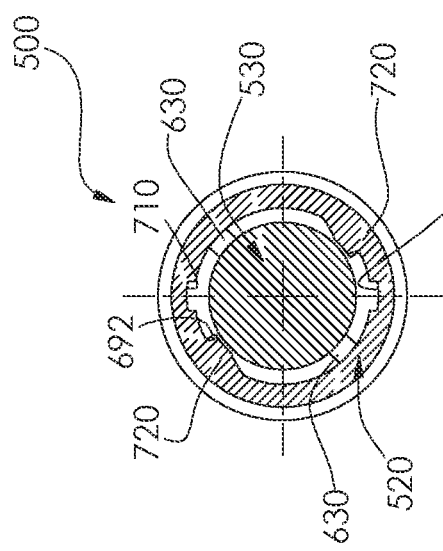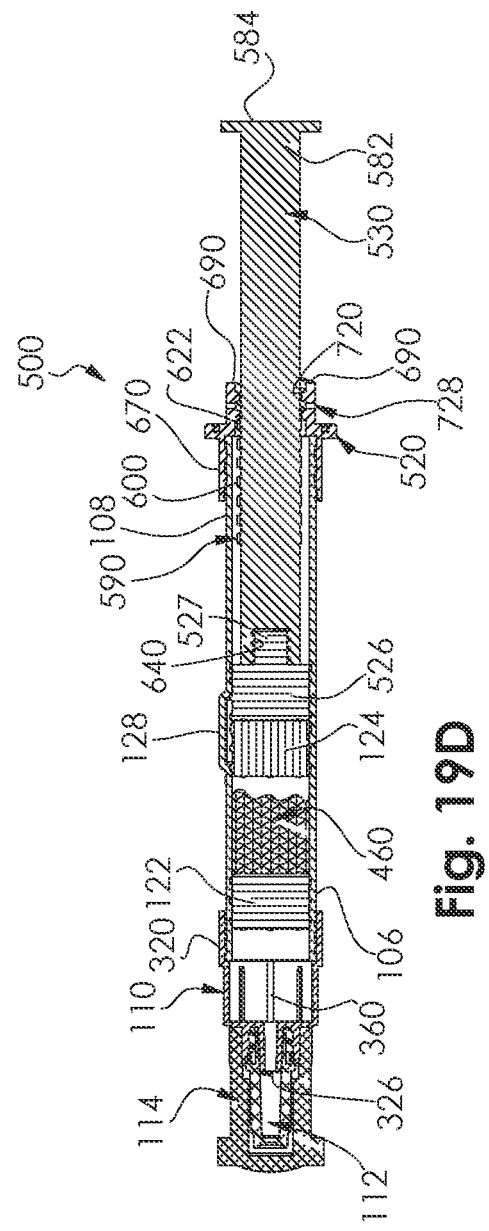

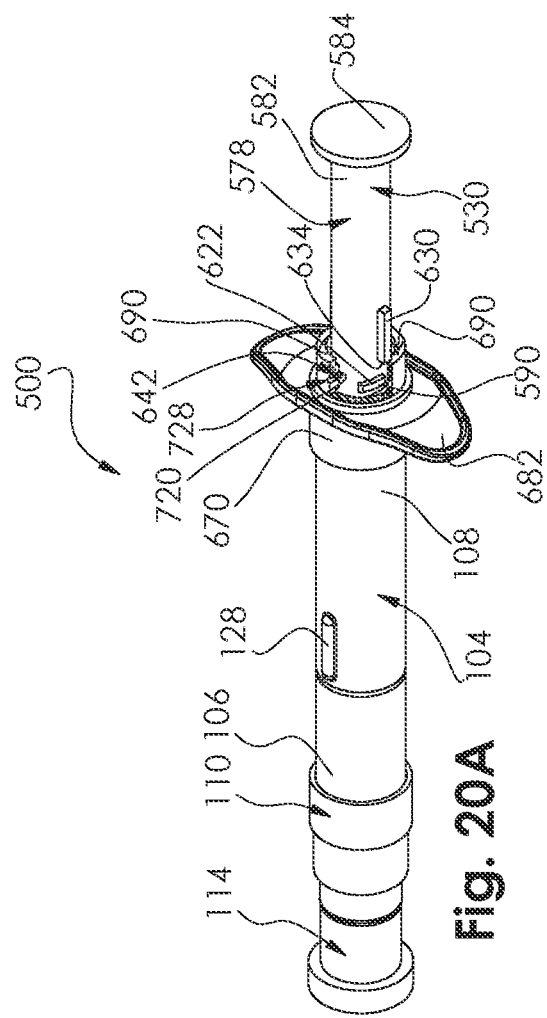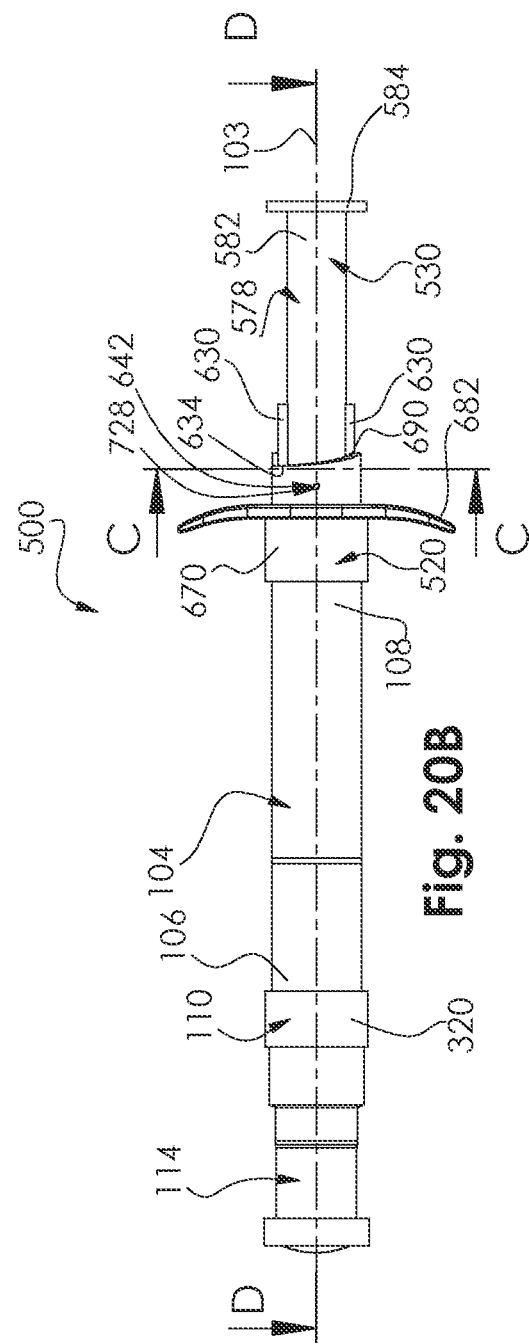

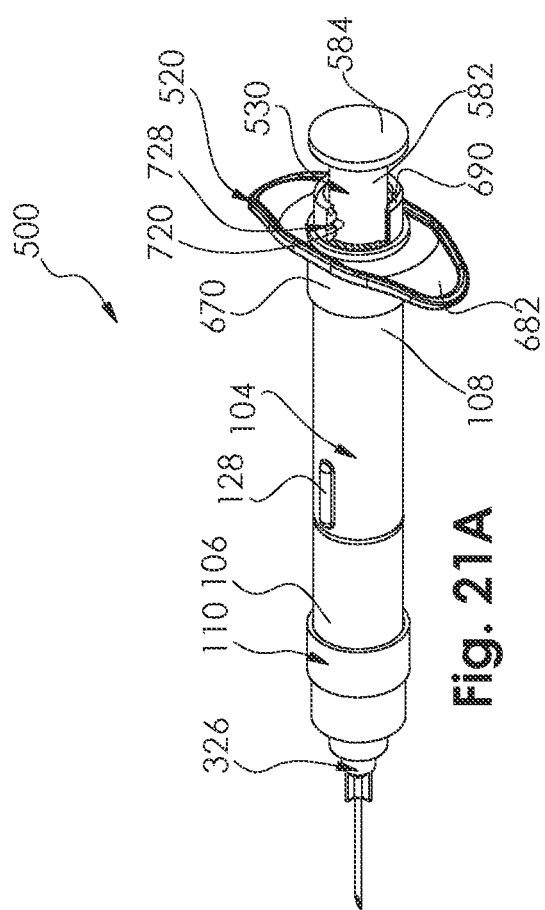
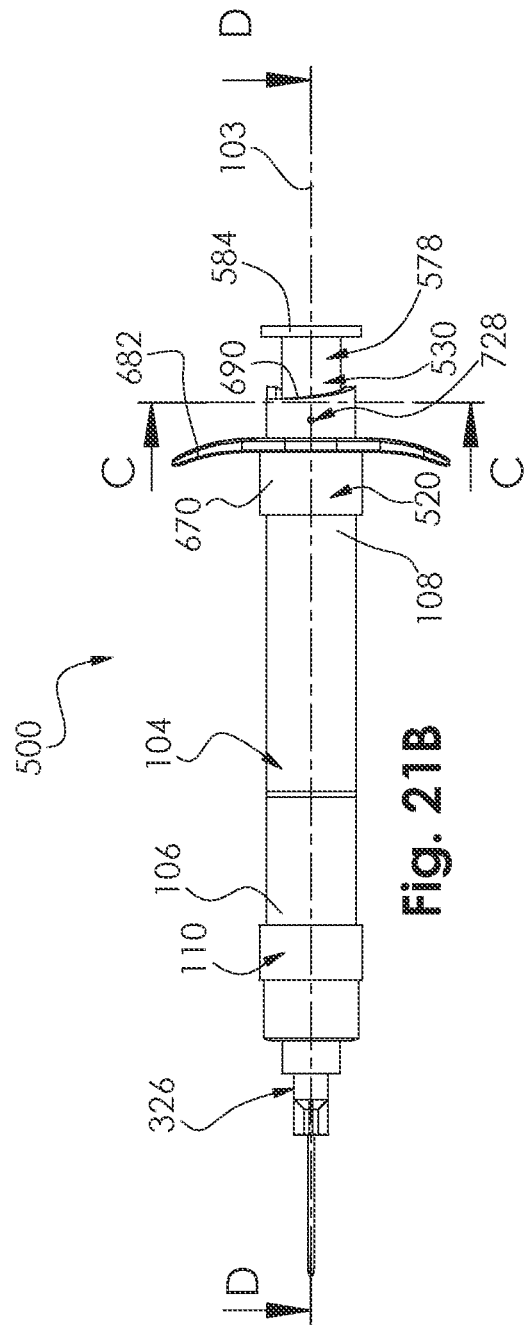
Fig. 21A
Fig. 21B

DUAL CHAMBER SYRINGE AND METHODS OF USE THEREOF

FIELD OF THE INVENTION

The present invention generally relates to a dual chamber syringe, and more specifically to a pre-fillable dual chamber syringe and methods of use thereof for reconstitution and injection of a medicament.

BACKGROUND OF THE INVENTION

Pre-fillable dual chamber syringes are known in the art for separately containing a powder/liquid medicament preparation and a solvent in different chambers of the syringe.

It is also known that pre-fillable dual chamber syringes preferably include a syringe barrel with several pistons, which are slidably sealingly disposed therewithin and divide the syringe barrel into several separate chambers, whereas one of the chambers contains a powder medicament and another contains a solvent. Alternatively, both chambers may include liquids that are stored separately and that shall be mixed only at the time of injection.

The pre-fillable dual chamber syringes also include a plunger rod, which is operative to engage one of the pistons. Upon displacement of the plunger rod relative to the syringe barrel, the pistons are advanced within the syringe barrel and permit reconstitution of the medicament by mixing the powder medicament with the solvent using a bypass formed in the syringe barrel.

SUMMARY OF THE INVENTION

The present invention seeks to provide a dual chamber syringe.

There is thus provided in accordance with an embodiment of the present invention or a combination of embodiments thereof a dual chamber syringe, comprising: a syringe barrel having a forward end, a rearward end and at least one bypass protrusion arranged along the longitudinal extent of the syringe barrel; a finger grip element coupled to the rearward end of the syringe barrel, the finger grip comprises at least one protrusion extending radially inwardly from an inner surface thereof; a plunger rod operatively coupled with the finger grip element; a guiding track is formed on the plunger rod and comprises a helical track portion and a longitudinal track portion; and wherein upon relative displacement of the plunger rod and the finger grip element, the at least one protrusion is guided along the guiding track.

Preferably, the helical track portion is connected to the longitudinal track portion. Further preferably, the helical track portion is connected to the longitudinal track portion by a raised ridge, whereas a step is formed between the helical track portion and the longitudinal track portion. Still further preferably, the plunger rod is configured to be threadably displaced relative to the finger grip element when the at least one protrusion is engaged with the helical track portion and the plunger rod is configured to be axially displaced relative to the finger grip element when the at least one protrusion is engaged with the longitudinal track portion.

In accordance with an embodiment of the present invention, the dual chamber syringe also comprising a forward piston, an intermediate piston and a rearward piston slidably arranged within the syringe barrel and wherein the rearward piston is threadably attached to the plunger rod.

Preferably, the plunger rod is configured to be axially displaced relative to the finger grip element when at least a portion of the intermediate piston is displaced forwardly of the at least one bypass protrusion. Further preferably, the plunger rod includes an inner plunger rod portion fixedly connected to an outer plunger rod portion and wherein the guiding track is formed on the outer plunger rod portion. Still further preferably, the inner plunger rod portion includes an externally threaded protrusion extending from a forward end thereof and the rearward piston includes an internally threaded socket adapted for threadable engagement with the externally threaded protrusion. Yet further preferably, the threading between the plunger rod and the rearward piston and the threading between the plunger rod and the finger grip element are different either in pitch or direction.

In accordance with another embodiment of the present invention, a dual chamber syringe, comprising: a syringe barrel having a forward end, a rearward end and at least one bypass protrusion arranged along the longitudinal extent of the syringe barrel; a finger grip element coupled to the rearward end of the syringe barrel, the finger grip comprises an inner threaded portion on an inner surface thereof and a rearward edge having at least one helical portion; a plunger rod operatively coupled with the finger grip element; the plunger rod comprises at least one threaded portion formed on an outer surface thereof and at least one guiding rib, which is rearwardly spaced from the at least one threaded portion; and wherein following relative displacement between the plunger rod and the finger grip element guided by engagement between the at least one threaded portion and the internally threaded portion, the at least one guiding rib is adapted to engage the at least one helical portion of the rearward edge.

Preferably, a guiding groove is formed on an inner surface of the finger grip element, and the guiding groove is radially spaced from the internally threaded portion. Further preferably, the plunger rod is configured to be threadably displaced in a first rotational direction relative to the finger grip element upon engagement of at least one threaded portion of the plunger rod with the internally threaded portion of the finger grip element and wherein the plunger rod is configured to be axially displaced relative to the finger grip element following engagement of the at least one guiding rib with the at least one helical portion of the rearward edge and application of sufficient force for guiding the at least one guiding rib into engagement with the guiding groove.

Still further preferably, rotation of the plunger rod relative to the finger grip element in a second rotational direction, opposite to the first rotational direction, is prevented due to engagement of the at least one guiding rib within the guiding groove. Yet further preferably, the at least one guiding rib has a tapered forwardly facing edge.

In accordance with an embodiment of the present invention, the dual chamber syringe also comprising a forward piston, an intermediate piston and a rearward piston slidably arranged within the syringe barrel and wherein the rearward piston is threadably attached to the plunger rod. Preferably, the plunger rod is configured to be axially displaced relative to the finger grip element when at least a portion of the intermediate piston is displaced forwardly of the at least one bypass protrusion. Further preferably, the plunger rod includes an internally threaded socket at the forward end thereof and the rearward piston includes an externally threaded protrusion extending rearwardly therefrom and adapted for threadable engagement with the internally threaded protrusion. Yet further preferably, the threading between the plunger rod and the rearward piston and the threading between the plunger rod and the finger grip element are different either in pitch or direction.

In accordance with an embodiment of the present invention, the slope of the at least one helical edge portion is different than the slope of the inner threaded portion of the finger grip element. Preferably, the slope of the at least one helical edge portion is smaller than the slope of the inner threaded portion of the finger grip element.

BRIEF DESCRIPTION OF THE DRAWINGS

The present invention will be understood and appreciated more fully from the following detailed description, taken in conjunction with the drawings in which:

FIGS. 2A and 2B are respectively a simplified perspective view and planar side view of a plunger rod inner portion forming part of the dual chamber syringe of FIGS. 1A & 1B;

FIGS. 3A, 3B, 3C, 3D and 3E are respectively a simplified perspective view, two simplified plan side views and two simplified sectional views taken along lines D-D and E-E in FIG. 3C of a plunger rod outer portion forming part of the dual chamber syringe of FIGS. 1A & 1B;

FIGS. 4A, 4B, 4C and 4D are respectively two simplified perspective views, a simplified plan side views and a simplified sectional view taken along lines D-D in FIG. 4C of a finger grip element forming part of the dual chamber syringe of FIGS. 1A & 1B;

FIGS. 5A, 5B, 5C and 5D are respectively two simplified perspective views, a simplified plan side views and a simplified sectional view taken along lines D-D in FIG. 5C of a luer lock element forming part of the dual chamber syringe of FIGS. 1A & 1B;

FIGS. 6A, 6B and 6C are respectively a simplified perspective view, a simplified plan side view and a simplified sectional view taken along lines C-C in FIG. 6B of an outer cap element forming part of the dual chamber syringe of FIGS. 1A & 1B;

FIGS. 8A, 8B, 8C and 8D are simplified drawings of the dual chamber syringe of FIGS. 1A-7C in a storage operative orientation, including respectively a simplified perspective view, a partially cut-out perspective view and two simplified sectional views taken along orthogonal lines C-C and D-D in FIG. 8B;

FIGS. 9A, 9B, 9C and 9D are simplified drawings of the dual chamber syringe of FIGS. 1A-7C in a pre-reconstitution operative orientation, including respectively a simplified perspective view, a partially cut-out perspective view and two simplified sectional views taken along orthogonal lines C-C and D-D in FIG. 9B;

FIGS. 10A, 10B, 10C and 10D are simplified drawings of the dual chamber syringe of FIGS. 1A-7C in a medicament reconstitution operative orientation, including respectively a simplified perspective view, a partially cut-out perspective view and two simplified sectional views taken along orthogonal lines C-C and D-D in FIG. 10B;

FIGS. 11A, 11B, 11C and 11D are simplified drawings of the dual chamber syringe of FIGS. 1A-7C in an end of medicament reconstitution operative orientation, including respectively a simplified perspective view, a partially cut-out perspective view and two simplified sectional views taken along orthogonal lines C-C and D-D in FIG. 11B;

FIGS. 12A, 12B, 12C and 12D are simplified drawings of the dual chamber syringe of FIGS. 1A-7C in an end of injection operative orientation, including respectively a simplified perspective view, a partially cut-out perspective view and two simplified sectional views taken along orthogonal lines C-C and D-D in FIG. 12B;

FIGS. 14A, 14B and 14C are respectively a simplified perspective view, a simplified plan side view and a simplified sectional view taken along lines C-C in FIG. 14B of a plunger rod forming part of the dual chamber syringe of FIGS. 13A & 13B;

FIGS. 15A, 15B and 15C are respectively a simplified perspective view, a simplified plan side view and a simplified sectional view taken along lines C-C in FIG. 15B of a finger grip element forming part of the dual chamber syringe of FIGS. 13A & 13B;

FIGS. 16A, 16B, 16C and 16D are simplified drawings of the dual chamber syringe of FIGS. 13A-15C in a storage operative orientation, including respectively a simplified partially cut-out perspective view, a simplified side plan view and two simplified sectional views taken along orthogonal lines C-C and D-D in FIG. 16B;

FIGS. 17A, 17B, 17C and 17D are simplified drawings of the dual chamber syringe of FIGS. 13A-15C in a pre-reconstitution operative orientation, including respectively a simplified partially cut-out perspective view, a simplified side plan view and two simplified sectional views taken along orthogonal lines C-C and D-D n FIG. 17B;

FIGS. 18A, 18B, 18C and 18D are simplified drawings of the dual chamber syringe of FIGS. 13A-15C in a medicament reconstitution operative orientation, including respectively a simplified partially cut-out perspective view, a simplified side plan view and two simplified sectional views taken along orthogonal lines C-C and D-D in FIG. 18B;

FIGS. 19A, 19B, 19C and 19D are simplified drawings of the dual chamber syringe of FIGS. 13A-15C in a prior to an end of medicament reconstitution operative orientation, including respectively a simplified partially cut-out perspective view, a simplified side plan view and two simplified sectional views taken along orthogonal lines C-C and D-D in FIG. 19B;

FIGS. 20A, 20B, 20C and 20D are simplified drawings of the dual chamber syringe of FIGS. 13A-15C in an end of reconstitution operative orientation, including respectively a simplified partially cut-out perspective view, a simplified side plan view and two simplified sectional views taken along orthogonal lines C-C and D-D in FIG. 20B;

FIGS. 21A, 21B, 21C and 21D are simplified drawings of the dual chamber syringe of FIGS. 13A-15C in an end of injection operative orientation, including respectively a simplified partially cut-out perspective view, a simplified side plan view and two simplified sectional views taken along orthogonal lines C-C and D-D in FIG. 20B.

DESCRIPTION OF EMBODIMENTS

Figure 1A:
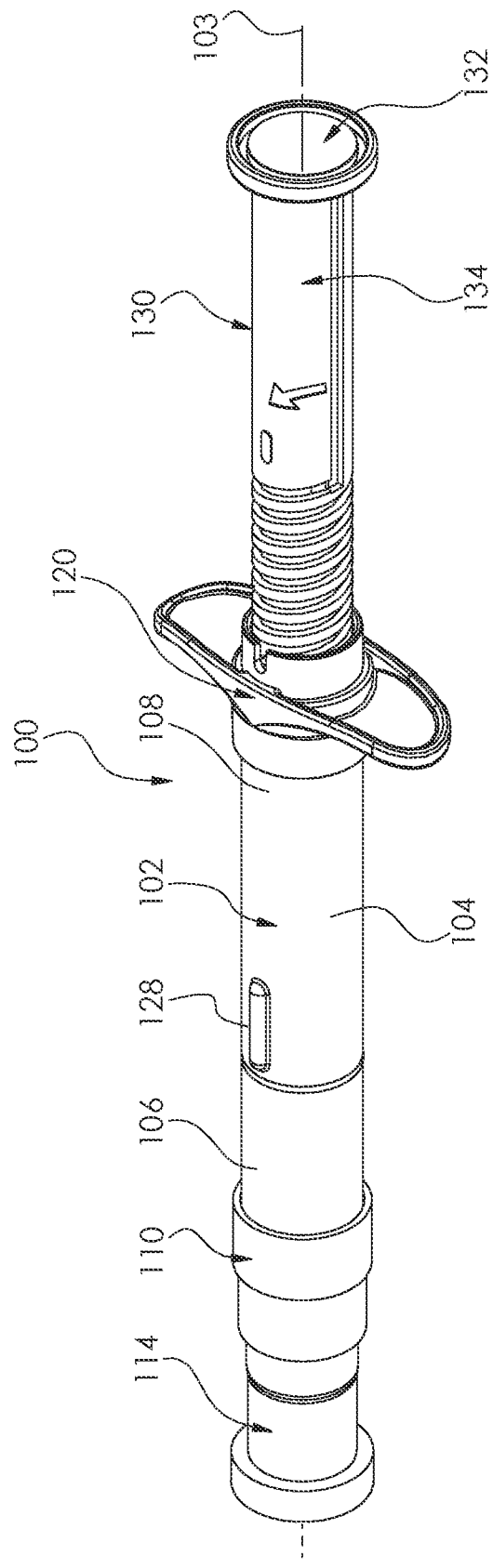
FIGS. 1A and 1B are respectively simplified pictorial view and exploded view of a dual chamber syringe constructed and operative in accordance with an embodiment of the present invention.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

Figure 1B:
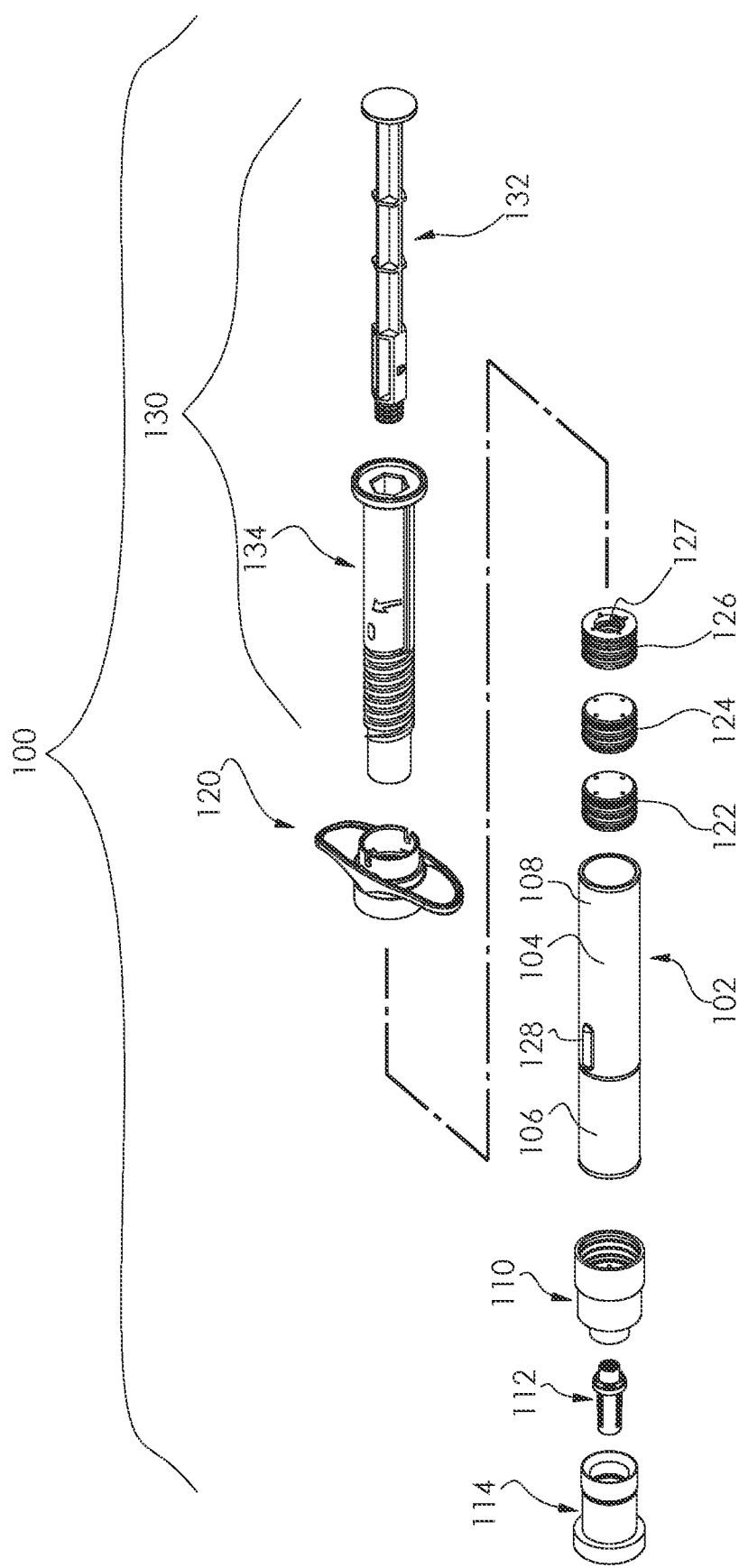

Reference is now made to FIGS. 1A and 1B, which are respectively simplified pictorial view and exploded view of a dual chamber syringe constructed and operative in accordance with an embodiment of the present invention.

As seen in FIGS. 1A & 1B, a dual chamber syringe 100 preferably includes a syringe assembly 102 arranged along a longitudinal axis 103. The syringe assembly 102 has a syringe barrel 104 having a forward end 106 and a rearward end 108. A luer lock element 110 is preferably fixedly and sealingly connected to the proximal end 106 of the syringe barrel 104. An inner cap element 112, which is adapted to seal and protect a portion of the luer lock element 110, and an outer cap 114 are preferably removably coupled to a forward end of the luer lock element 110.

It is also seen in FIGS. 1A & 1B that a finger grip 120 is fixedly connected to the rearward end 108 of the syringe barrel 104. The syringe assembly 102 also preferably includes three pistons, namely a forward piston 122, an intermediate piston 124 and a rearward piston 126, which are contained within the syringe barrel 104 and are adapted for slidable axial displacement relative to the syringe barrel 104. It is appreciated that a drug preparation is preferably confined between one pair of the pistons and a solvent is preferably confined between another pair of the pistons and upon appropriate longitudinal displacement of the pistons, the two substances are configured for reconstitution and subsequent ejection, as described in detail hereinbelow. It is noted that the rearward piston 126 includes an internally threaded socket 127, which extends forwardly from a rearward end of the rearward piston 126.

It is also noted that the rearward piston 126 can alternatively include a rearwardly extending externally threaded protrusion. Further alternatively, the rearward piston 126 may include snap protrusions or recesses or any other suitable coupling means.

The syringe barrel 104 is preferably made of glass. The syringe barrel has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod assembly 130 preferably includes a plunger rod inner portion 132 and a plunger rod outer portion 134, which are preferably fixedly coupled with each other upon insertion of the plunger rod inner portion 132 into the plunger rod outer portion 134. Alternatively, the plunger rod assembly 130 may be an integrally formed element or split in any other way suitable for manufacturing.

It is a particular feature of an embodiment of the present invention that the plunger rod assembly 130 is operatively associated with the finger grip 120 and is displaceable with respect thereto and thus, with respect to the syringe barrel 104. In certain operative orientations, the plunger rod assembly 130 is rotatable about longitudinal axis 103 with respect to the finger grip 120 and the syringe barrel 104. In other operative orientations, the plunger rod assembly 130 is axially displaceable along longitudinal axis 103 relative to said finger grip 120 and the syringe barrel 104.

Reference is now made to FIGS. 2A and 2B, which are respectively a simplified perspective view and planar side view of the plunger rod inner portion 132 forming part of the dual chamber syringe 100 of FIGS. 1A & 1B.

The plunger rod inner portion 132 preferably is an integrally formed element, preferably injection molded of plastic and is arranged along longitudinal axis of symmetry 103.

The plunger rod inner portion 132 preferably includes a longitudinal shaft 150 terminating at a generally circular flange 152 at a rearward end 154 thereof. The circular flange 152 extends generally radially outwardly from the outer surface of the longitudinal shaft 150 and is disposed generally transversely with respect thereto. A generally widened longitudinal portion 156 extends forwardly from a forward end 158 of the longitudinal shaft 150 and an externally threaded protrusion 160 extends forwardly from a forward end 162 of the widened longitudinal portion 156.

Typically, two diametrically opposed snap protrusions 164 are formed on two opposite sides of the widened longitudinal portion 156. Snap protrusions 164 generally extend radially outwardly from the widened longitudinal portion 156 and are adapted for fixedly connecting the plunger rod inner portion 132 with the plunger rod outer portion 134. Each of the snap protrusions 164 preferably includes a rearwardly facing surface 166, which is disposed generally transversely with respect to the longitudinal axis 103.

Reference is now made to FIGS. 3A, 3B, 3C, 3D and 3E, which are respectively a simplified perspective view, two simplified plan side views and two simplified sectional views taken along lines D-D and E-E in FIG. 3C of the plunger rod outer portion 134 forming part of the dual chamber syringe 100 of FIGS. 1A & 1B.

The plunger rod outer portion 134 preferably is an integrally formed generally cylindrical hollow element, preferably injection molded of plastic and is arranged along longitudinal axis of symmetry 103.

The plunger rod outer portion 134 has a longitudinal shaft 178, which preferably includes a longitudinal rearward portion 180, terminating at a generally circular flange 182 at a rearward end 184 thereof. The circular flange 182 extends generally radially outwardly from the outer surface of the rearward portion 180 and is disposed generally transversely with respect thereto. The rearward portion 180 has a forward end 186, from which an intermediate externally threaded portion 190 extends forwardly up to a forward portion 192, terminating at a forwardmost circumferential edge 194. It is noted that the outer diameter of the rearward portion 180 is somewhat greater than the outer diameter of the forward portion 192.

The plunger rod outer portion 134 has an outer surface 195 and an inner surface 196, formed by a longitudinal through bore 198.

It is a particular feature of an embodiment of the present invention that a guiding track 200 is formed on the outer surface 195 of the plunger rod outer portion 134. The guiding track 200 includes a longitudinal track portion 202 and a helical track portion 204 connected thereto by a raised ridge 206. It is particularly seen in FIGS. 3B, 3C and 3E that the longitudinal track portion 202 is formed as a longitudinal groove formed in the rearward portion 180 and extends from the rearward end 184 preferably to the forward end 186 thereof. The helical track portion 204 is preferably formed as a helical groove that forms part of the externally threaded portion 190 and is defined by the track of the thread thereof. It is specifically seen in FIGS. 3B and 3C that the helical track portion 204 and the longitudinal track portion 202 form a continuous guiding track 200 by means of raised ridge 206, which connects the two track portions 202 and 204. It is noted that typically two longitudinal track portions 202 are formed on the rearward portion 180 and connect with the helical track portion 204 through raised ridge 206. The two longitudinal track portions 202 are typically diametrically opposed with respect to each other. It is also noted that alternatively any number of longitudinal track portions 202 can be formed on the rearward portion 180 in accordance with an embodiment of the present invention.

It is noted that raised ridge 206 extends radially outwardly with respect to longitudinal track portion 202, thus forming a radially facing shoulder 210 between the helical track portion 204 and the longitudinal track portion 202.

The helical track portion 204 has a forward end 220 and a rearward end 222, adjacent the raised ridge 206. The forward end 220 preferably includes a rearwardly facing tapered surface 223. The longitudinal track portion 202 has a forward end 224 and a rearward end 226 adjacent the circular flange 182.

It is noted that the raised ridge 206 may be located at the rearward end 222 of the helical track portion 202. Alternatively, the entire helical track portion 204 may have an outer diameter that is slightly larger than the outer dimeter defined by the longitudinal track portions 202. In this case, the helical track portion 204 extends radially outwardly with respect to longitudinal track portion 202, thus forming the radially facing shoulder 210 between the helical track portion 204 and the longitudinal track portion 202 while obviating the raised ridge 206.

It is seen in FIGS. 3B and 3D that an internal socket 240 is formed within circular flange 182, having a rearwardly facing surface 242 and adapted for receiving circular flange 152 of the plunger rod inner portion 132 and supporting thereof for preventing forward axial displacement of the plunger rod inner portion 132 relative to the plunger rod outer portion 134. The internal socket 240 communicated with the longitudinal through bore 198, which terminates at a forward bore portion 244, having a slightly greater diameter than through bore 198, thus forming a forwardly facing shoulder 246 between the two bores. The forwardly facing shoulder 246 is adapted for engaging snap protrusions 164 of the plunger rod inner portion 132 and thus prevent rearward axial displacement of the plunger rod inner portion 132 relative to the plunger rod outer portion 134.

It is appreciated that alternatively, the engaging snap protrusion 164 might be located on the plunger rod outer portion 134 while engaging with a forwardly facing shoulder located on the plunger rod inner portion 132, thus preventing the plunger rod inner portion 132 from rearward axial displacement relative to the plunger rod outer portion 134.

It is appreciated that alternatively the plunger rod assembly 130 may be formed as a single integrally made element, without fixedly connecting plunger rod inner and outer portions.

It is noted that an indication for the direction of rotation of the plunger rod assembly 130 is preferably provided on the outer surface 194 of the plunger rod outer portion 134, such as arrow 250.

It is further noted that an indication for end of plunger rod rotation is provided on the outer surface 194 of the plunger rod outer portion 134, such as at least one protrusion 252, that is preferably disposed rearwardly of rearward end 222 of the guiding track 200. It is noted that alternatively, an indication for end of plunger rod rotation can be provided by a marking placed on the outer surface 194 of the plunger rod outer portion 134.

Reference is now made to FIGS. 4A, 4B, 4C and 4D, which are respectively two simplified perspective views, a simplified plan side views and a simplified sectional view taken along lines D-D in FIG. 4C of the finger grip element 120 forming part of the dual chamber syringe 100 of FIGS. 1A & 1B.

The finger grip element 120 preferably is an integrally formed partially cylindrical hollow element, preferably injection molded of plastic and is arranged along longitudinal axis of symmetry 103.

The finger grip element 120 has a generally cylindrical base portion 270 having an outer surface 272 and an inner surface 274, defined by a through bore 276. The base portion 270 has a rearward circumferential edge 278 and a forward circumferential edge 280. Typically, two finger grip portions 282 extend generally transversely radially outwardly from base portion 270. The two finger grip portions 282 preferably extend in mutually opposite radial directions.

The through bore 276 has a rearward bore portion 290 and a forward bore portion 292 extending forwardly therefrom. The inner diameter of the base portion 270 that is defined by rearward bore portion 290 is slightly smaller than the inner diameter of the base portion 270 defined by forward bore portion 292. Typically, several circumferential rims 294 extend radially inwardly from the inner surface 274 of the base portion 270 at the forward bore portion 292. Circumferential rims 294 are adapted for pressure-fit engagement with the syringe barrel 104.

A generally circumferential forwardly facing shoulder 296 is formed between the rearward bore portion 290 and the forward bore portion 292.

Typically, two mutually opposed guided teeth 300 are formed on the inner surface 274 of the base portion 270 at the rearward bore portion 290, preferably adjacent the forwardly facing shoulder 296. The guided teeth 300 extend generally radially inwardly from the inner surface 274 of the base portion 270. It is noted that the forwardly and rearwardly facing surfaces of teeth 300 are preferably disposed at an angle with respect to longitudinal axis 103 to fit in the corresponding helical track portion 204 of the plunger rod outer portion 134. Additionally, a side wall of the teeth 300 is preferably forwardly tapered to facilitate engagement of the teeth 300 with the tapered surface 223 of the threaded portion 190.

It is noted that alternatively the radially inwardly extending guided teeth can be of a generally cylindrical shape and a circular cross-section of such cylindrical guided teeth preferably also facilitates engagement thereof with the tapered surface 223 of the threaded portion 190.

It is further noted that at least one recess 302 is formed in base portion 270, generally extending slightly forwardly from the rearward circumferential edge 278 thereof.

Reference is now made to FIGS. 5A, 5B, 5C and 5D, which are respectively two simplified perspective views, a simplified plan side views and a simplified sectional view taken along lines D-D in FIG. 5C of the luer lock element 110 forming part of the dual chamber syringe 100 of FIGS. 1A & 1B.

The luer lock element 110 preferably is an integrally formed partially cylindrical hollow element, preferably injection molded of plastic and is arranged along longitudinal axis of symmetry 103.

The luer lock element 110 has a rearward portion 320 having a first outer dimeter, an intermediate portion 322 extending forwardly therefrom and having a second outer diameter, slightly smaller than the first outer diameter and a forward portion 324, extending forwardly from the intermediate portion and having a third outer diameter, which is slightly smaller than the second outer dimeter.

The rearward portion 320 has a rearward most circumferential edge 330 and the intermediate portion 322 has a partially closed forward end 332 connecting the intermediate portion 322 with the forward portion 324. A male luer 326 extends forwardly from forward end 332 and is coaxially disposed with and partially encircled by the forward portion 322. The forward portion 324 has an internal threading 334 and terminates at a generally inwardly directed undercut protrusions 336 formed adjacent a forward end of the forward portion 324. The undercut protrusions 336 may also be formed as a circumferential rim extending radially inwardly from the forward end of the forward portion 324.

A through bore 340 is formed within the luer lock element 110 and extends axially therethrough. The through bore 340 has a rearward portion 342 and an intermediate portion 344. Luer bore 346 is formed in male luer 326 and is adapted to fluidly communicate with intermediate portion 344 of through bore 340.

Rearward inner surface 350 is defined by the rearward portion 342 and intermediate inner surface 352 is defined by the intermediate portion 344. Typically, several circumferential rims 354 extend radially inwardly from the inner surface 350 of the rearward portion 320. Circumferential rims 354 are adapted for pressure-fit engagement with the forward end 106 of the syringe barrel 104.

Typically, several longitudinal grooves 360, radially spaced from each other, are formed along at least a portion of the longitudinal extent of inner surface 352. Each of the grooves 360 preferably extends from inner surface 352 to a rearwardly facing surface 362 of the forward end 332.

Additionally, it is specifically seen in FIG. 5D that several longitudinal ribs 364, radially spaced from each other and radially spaced from grooves 360, are formed along at least a portion of the longitudinal extent of inner surface 352.

Reference is now made to FIGS. 6A, 6B and 6C, which are respectively a simplified perspective view, a simplified plan side view and a simplified sectional view taken along lines C-C in FIG. 6B of the outer cap element 114 forming part of the dual chamber syringe 100 of FIGS. 1A & 1B.

The outer cap element 114 preferably is an integrally formed partially cylindrical hollow element, preferably injection molded of plastic and is arranged along longitudinal axis of symmetry 103.

The outer cap element 114 preferably has a longitudinal base portion 380 and an outwardly radially extending generally circular gripping flange 382 formed at a forward end of base portion 380. The base portion 380 has a generally circular forwardly tapered edge 384 and a longitudinal bore 386 extending forwardly therefrom toward the circular gripping flange 382 and defining a rearwardly facing surface 388.

Longitudinal bore 386 preferably has a forward portion 390 of a first diameter adjacent rearwardly facing surface 388 and a rearward portion 392 of a second diameter, generally larger than the first diameter, adjacent forwardly tapered edge 384. A rearwardly tapered shoulder 394 is formed between the forward portion 390 and the rearward portion 392 of longitudinal bore 386.

Figure 7C:
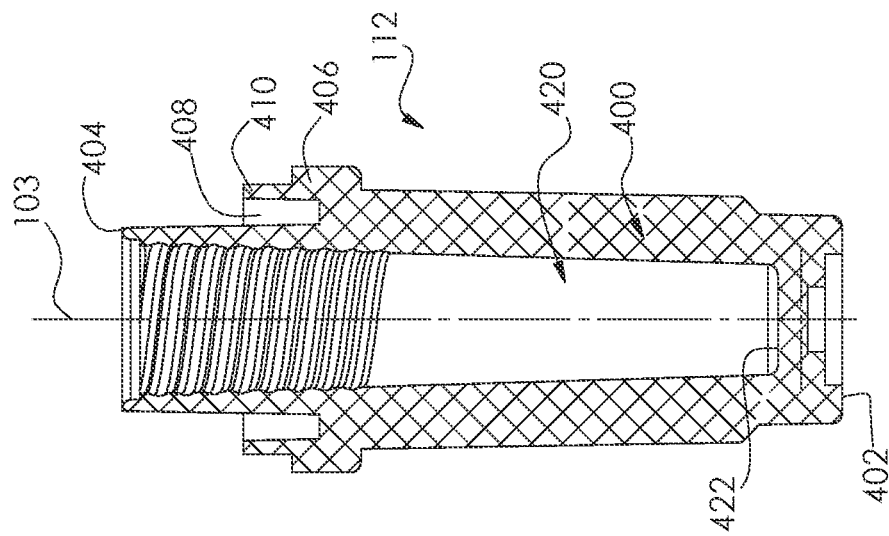
FIGS. 7A, 7B and 7C are respectively a simplified perspective view, a simplified plan side view and a simplified sectional view taken along lines C-C in FIG. 7B of an inner cap element forming part of the dual chamber syringe of FIGS. 1A & 1B.
Figure 7B:
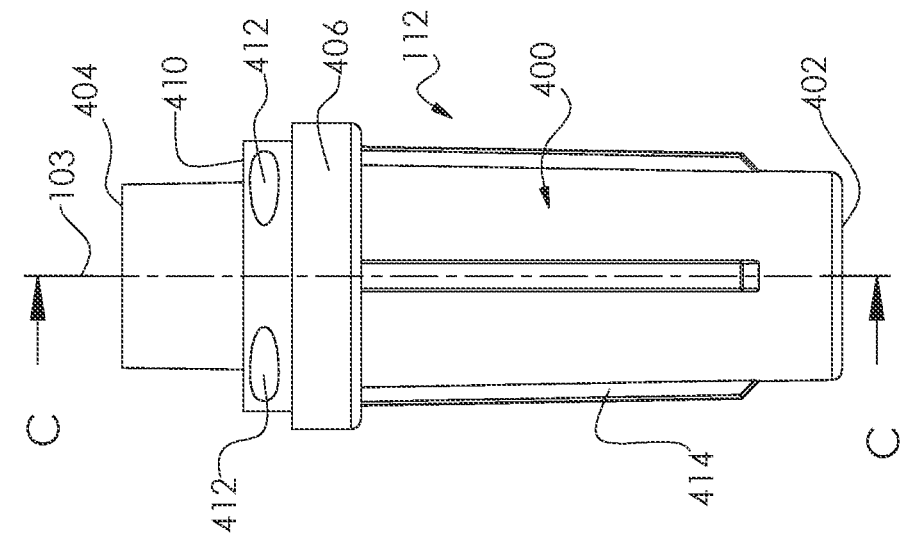
Figure 7A:
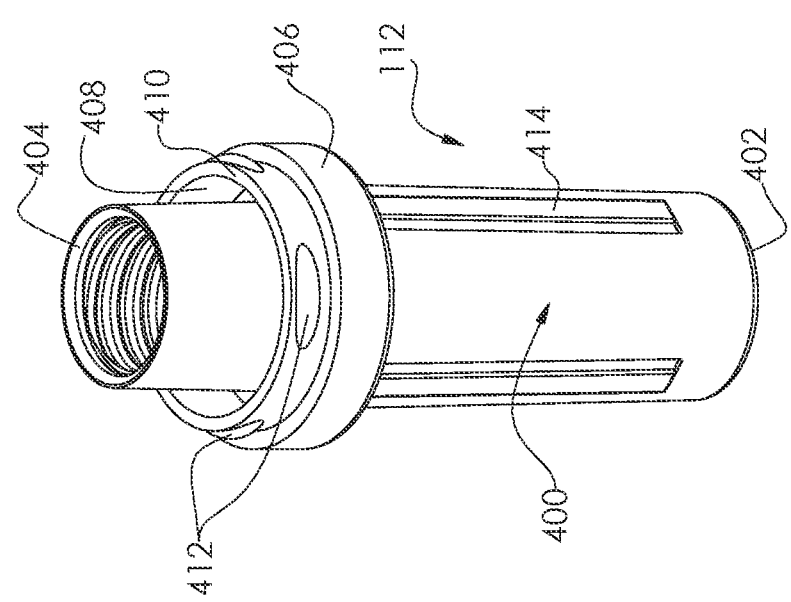

Reference is now made to FIGS. 7A, 7B and 7C, which are respectively a simplified perspective view, a simplified plan side view and a simplified sectional view taken along lines C-C in FIG. 7B of the inner cap element 112 forming part of the dual chamber syringe 100 of FIGS. 1A & 1B.

The inner cap element 112 preferably is an integrally formed partially cylindrical hollow element, preferably injection molded of plastic and is arranged along longitudinal axis of symmetry 103.

The inner cap element 112 preferably has a longitudinal base portion 400 having a forward end 402 and a rearward end 404. A generally circular radially outwardly extending flange 406 is formed generally adjacent the rearward end 404 thereof. A circumferential socket 408 is formed at flange 406 and extends forwardly from a forward edge 410 of the flange 406. Typically, a plurality of outwardly facing protrusions 412 are formed on an outer circumference of a portion of the flange 406 and are disposed preferably adjacent forward edge 410. Outwardly facing protrusions 412 are adapted for pressure fit engagement with undercut protrusions 336 of the luer lock element 110. A plurality of reinforcing ribs 414 are formed on the outer surface of the base portion 400 and are mutually radially spaced from each other.

A bore 420 is formed in base portion 400 and extends from rearward end 404 of the inner cap element 112 toward the forward end 402, forming a rearwardly facing surface 422 adjacent the forward end 402. An internal threading 424 is formed on an inner surface of the base portion 400 and extends from the rearward end 404 forwardly, along a portion of the longitudinal extent of the base portion 400.

Reference is now made to FIGS. 8A, 8B, 8C and 8D, which are simplified drawings of the dual chamber syringe 100 of FIGS. 1A-7C in a storage operative orientation, including respectively a simplified perspective view, a partially cut-out perspective view and two simplified sectional views taken along orthogonal lines C-C and D-D in FIG. 8B.

It is seen in FIGS. 8A-8D that the dual chamber syringe 100 is arranged along the longitudinal axis 103. The base portion 270 of the finger grip 120 is fixedly attached to the rearward end 108 of the syringe barrel 104 by means of pressure-fit engagement between rims 294 of the finger grip 120 and the outer surface of the syringe barrel 104.

The rearward portion 320 of the luer lock element 110 is fixedly attached to the forward end 106 of the syringe barrel 104 by means of pressure-fit engagement between rims 354 of the luer lock element 110 and the outer surface of the syringe barrel 104. It is seen that the intermediate portion 322 of luer lock element 110 is disposed forwardly of the forward end 106 of the syringe barrel 104, so that the longitudinal grooves 360 of the luer lock element 110 are also disposed forwardly of the forward end 106 of the syringe barrel 104. It is noted that the inner dimeter of the intermediate portion 322 is slightly larger than the inner diameter of the syringe barrel 104.

It is noted that alternatively, the syringe barrel 104 and the luer lock element 110 may be formed as an integral part. Further alternatively, a needle can be fixedly attached to the luer 326 of the luer lock element 110 or to a luer that is formed as part of the syringe barrel, in case the syringe barrel and the luer lock element are integrally formed.

The inner cap element 112 is releasably mounted over male luer 326 of the luer lock element 110 and is releasably held therein by means of engagement of undercut protrusions 336 of luer lock element 110 with protrusions 412 of the inner cap element 112. The outer cap element 114 surrounds the inner cap element 112 and is disposed in friction-fit engagement therewith. It is particularly seen that the inner cap element 112 is inserted into longitudinal bore 386 of the outer cap element 114 and the edge 384 of the outer cap element 114 is disposed adjacent or abutting with forward end 332 of the luer lock element 110.

It is additionally seen in FIGS. 8B and 8C that the forward piston 122 is sealingly slidably disposed with respect to the inner surface of the syringe barrel 104 and is located generally in proximity to the forward end 106 of the syringe barrel 104. The intermediate piston 124 is also sealingly slidably disposed with respect to the inner surface of the syringe barrel 104 and is located generally between the rearward end 108 of the syringe barrel 104 and between the bypass protrusion 128.

It is noted that drug preparation 440 is confined between the forward piston 122 and the intermediate piston 124 and the forward piston 122 is used for sealing the drug preparation 440 between the two pistons 122 and 124.

It is particularly seen in FIG. 8C that the plunger rod assembly 130 is threadably coupled to the rearward piston 126 by means of threadable interconnection between externally threaded protrusion 160 of plunger rod inner portion 132 with internally threaded socket 127 of the rearward piston 126.

It is noted that alternatively the plunger rod assembly 130 and the rearward piston 126 can be connected by means of threadable interconnection between externally threaded protrusion extending rearwardly from the rearward piston 126 and an internally threaded socket formed in the forward portion of the plunger rod assembly 130. Further alternatively, the plunger rod assembly 130 and the rearward piston 126 can be connected by means of snap coupling or any other suitable coupling means.

It is appreciated that the threading between the internally threaded socket 127 of the rearward piston 126 and the externally threaded protrusion 160 of the plunger rod assembly 130 may have a different pitch or direction than the threading between the externally threaded portion 190 of the plunger rod assembly 130 and the guiding teeth 300 of the finger grip element 120. These two different threadings are configured to prevent disengagement of the plunger rod assembly 130 from the rearward piston 126 in case the plunger rod assembly 130 is rotated inadvertently in an opposite rotational direction than the direction indicated by arrow 250.

It is noted that solvent 450 is confined between the rearward piston 126 and the intermediate piston 124.

The plunger rod inner portion 132 is inserted into the plunger rod outer portion 134 and is fixedly held therein, thereby forming the plunger rod assembly 130. It is noted that the flange 152 of the plunger rod inner portion 132 is supported against rearwardly facing surface 242 of the plunger rod outer portion 134 to prevent forward displacement of the plunger rod inner portion 132 relative to the plunger rod outer portion 134. It is further noted that the snap protrusions 164 of the plunger rod inner portion 132 are supported against forwardly facing shoulder 246 of the plunger rod outer portion 134 to prevent rearward displacement of the plunger rod inner portion 132 relative to the plunger rod outer portion 134.

It is a particular feature of an embodiment of the present invention that the plunger rod assembly 130 is operatively associated with the finger grip 120 and is displaceable with respect thereto and thus, with respect to the syringe barrel 104. In this storage operative orientation, the plunger rod assembly 130 is partially axially inserted into the syringe barrel 104, such that the teeth 300 of the finger grip 120 are not yet engaged with the guiding track 200 of the plunger rod outer portion 134.

It is particularly seen in FIGS. 8B-8D that the teeth 300 of finger grip 120 are disposed along the longitudinal extent of the forward portion 192 of the plunger rod outer portion 134 and are axially forwardly spaced with respect to the forward end 220 of the helical track portion 204 of the guiding track 200.

It is noted that in this storage operative orientation, the at least one protrusion 252 of the plunger rod outer portion 134 is rearwardly spaced from recess 302 of the finger grip element 120.

Figure 9C:
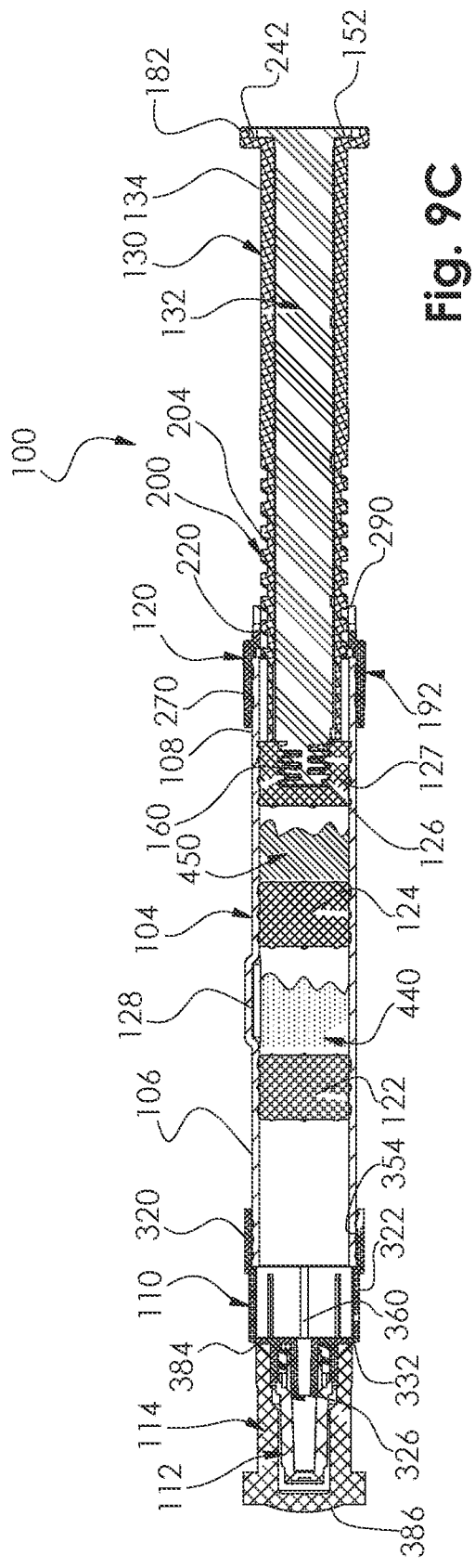

Reference is now made to FIGS. 9A, 9B, 9C and 9D, which are simplified drawings of the dual chamber syringe 100 of FIGS. 1A-7C in a pre-reconstitution operative orientation, including respectively a simplified perspective view, a partially cut-out perspective view and two simplified sectional views taken along orthogonal lines C-C and D-D in FIG. 9B.

It is seen in FIGS. 9A-9D that the plunger rod assembly 130 is preferably slightly axially forwardly displaced relative to the syringe barrel 104 along longitudinal axis 103 to compensate for dimension variations between the different components of the dual chamber syringe 100 and to compensate for piston displacement due to pressure variations within the syringe assembly 102, such as during shipping, for example. It is appreciated that the axial displacement of the plunger rod assembly 130 relative to the syringe barrel 104 may be minimal in this operative orientation.

Figure 9D:
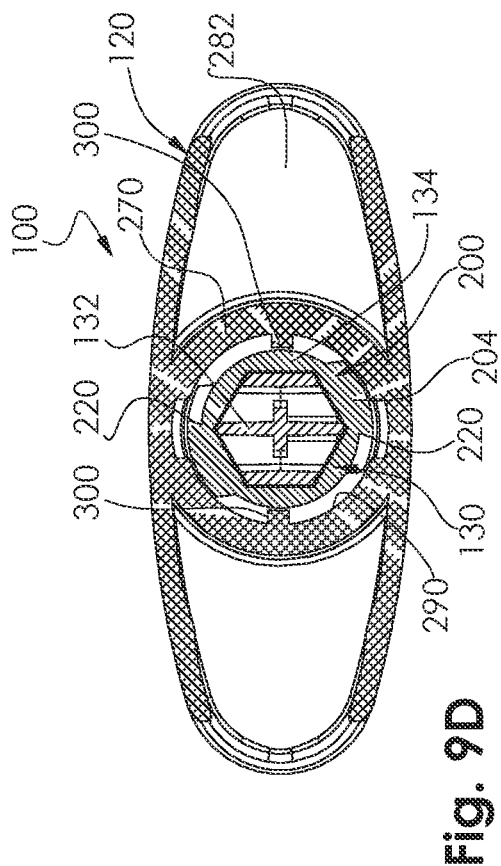

It is appreciated that all spatial relationships between the various components of the dual chamber syringe 100 remain the same as described hereinabove with respect to the storage operative orientation illustrated in FIGS. 8A-8D, besides the following spatial relationships:

It is particularly seen in FIGS. 9B-9D that in this pre-reconstitution operative orientation, the plunger rod assembly 130 is forwardly axially displaced up to engagement of the teeth 300 of finger grip 120 with the tapered surface 223 of the forward end 220 of the helical track portion 204 of the guiding track 200.

It is also seen in FIGS. 9B and 9C that the rearward piston 126 is forwardly axially displaced relative to the syringe barrel 104 along with the plunger rod assembly 130, due to the threadable engagement therebetween. The intermediate piston 124 and the forward piston 122 are correspondingly axially forwardly displaced relative to the syringe barrel 104 due to the hydraulic pressure created in the syringe chamber containing the solvent 450 and in the syringe chamber containing the drug preparation 440. It is noted that in this pre-reconstitution operative orientation, the intermediate piston 124 is still rearwardly spaced from the bypass protrusion 128 of the syringe barrel 104.

Figure 10C:
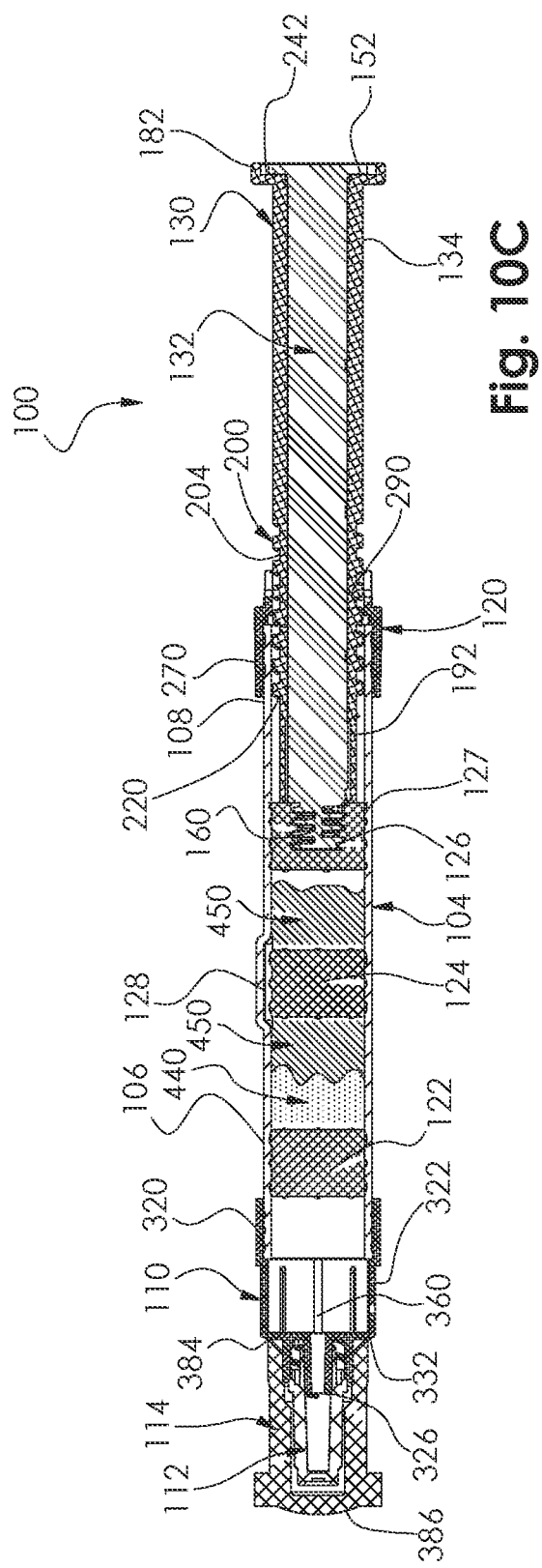
Figure 10D:
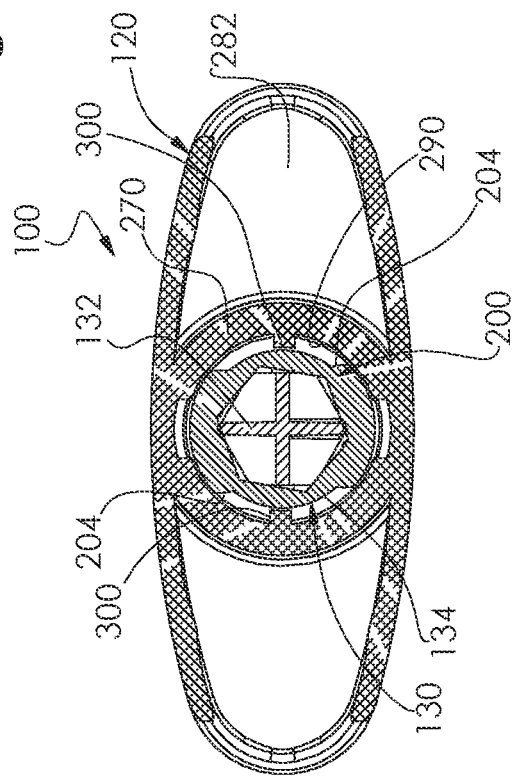

Reference is now made to FIGS. 10A, 10B, 10C and 10D, which are simplified drawings of the dual chamber syringe 100 of FIGS. 1A-7C in a medicament reconstitution operative orientation, including respectively a simplified perspective view, a partially cut-out perspective view and two simplified sectional views taken along orthogonal lines C-C and D-D in FIG. 10B.

It is seen in FIGS. 10A-10D that the plunger rod assembly 130 is axially forwardly advanced relative to the syringe barrel 104 by means of thread-like rotation of the plunger rod assembly 130 relative to the finger grip element 120. The plunger rod assembly 130 is rotated relative to the finger grip element 120 and thus relative to syringe barrel 104 about longitudinal axis 103 in the rotational direction indicated by arrow 250 and thereby longitudinally displaced forwardly along longitudinal axis 103 to provide for passage of solvent 450 into the chamber containing the drug preparation 440 through the bypass protrusion 128 of the syringe barrel 104 in order to reconstitute the drug preparation resulting in a liquid medicament solution contained between the forward piston 122 and the intermediate piston 124.

The dual chamber syringe 100 is shown during the medicament reconstitution in FIGS. 10A-10D, whereas only a portion of the solvent 450 passed into the chamber containing the drug preparation 440 through the bypass protrusion 128.

It is noted that the longitudinal dimension of the externally threaded portion 190 is preferably defined as the length that is required to axially displace the intermediate piston 124 toward the bypass protrusion 128 of the syringe barrel 104 and to axially displace the rearward piston 126 up to engagement with the intermediate piston 124.

It is appreciated that all spatial relationships between the various components of the dual chamber syringe 100 remain the same as described hereinabove with respect to the pre-reconstitution operative orientation illustrated in FIGS. 9A-9D, besides the following spatial relationships:

It is a particular feature of an embodiment of the present invention that as seen particularly in FIGS. 10A-10D, in this medicament reconstitution operative orientation, the plunger rod assembly 130 is rotated about the longitudinal axis and due to thread-like engagement of the teeth 300 of finger grip 120 with the helical track portion 204 of the guiding track 200 of the plunger rod assembly 130, the plunger rod assembly 130 is forwardly displaced longitudinally along longitudinal axis 103.

It is noted that in this medicament reconstitution operative orientation shown in FIGS. 10A-10D, the plunger rod assembly 130 completed only a portion of its forward longitudinal displacement required for complete medicament reconstitution. It is specifically seen that the teeth 300 of the finger grip element 120 are disposed at an intermediate location along the helical track portion 204 of the guiding track 200. The teeth 300 of the finger grip element 120 are now disposed between the forward end 220 and the rearward end 222 of the helical track portion 204.

It is seen in FIGS. 10B and 10C that the rearward piston 126 is forwardly axially displaced relative to the syringe barrel 104 along with the forward displacement of the plunger rod assembly 130, due to the threadable engagement therebetween.

It is a particular feature of an embodiment of the present invention that the rotational displacement of the plunger rod assembly 130 is translated to axial forward displacement thereof along longitudinal axis 103 due to thread-like engagement between the plunger rod assembly 130 and the finger grip element 120, specifically between the helical track portion 204 of the plunger rod assembly 130 and the teeth 300 of the finger grip element 120.

It is noted that upon initiation of axial forward displacement of the plunger rod assembly 130, all three pistons, namely the forward piston 122, the intermediate piston 124 and the rearward piston 126 are displaced together and remain at a constant distance one from another up until the point where the intermediate piston 124 is axially aligned with the bypass protrusion 128 of the syringe barrel 104. At this point, when the intermediate piston 124 is aligned with the bypass protrusion 128, fluid flow passage is established between the two chambers of the dual chamber syringe 100 and solvent 450 is transferred into the chamber containing the drug preparation 440 through the bypass protrusion 128.

Once the intermediate piston 124 is aligned with the bypass protrusion 128, the plunger rod assembly 130 along with the rearward piston 126 are forwardly displaced axially due to the thread-like engagement that is explained in detail hereinabove, toward the intermediate piston 124 until all solvent 450 is transferred into the chamber containing drug preparation 440.

It is noted that in this reconstitution operative orientation, the at least one protrusion 252 of the plunger rod outer portion 134 remains rearwardly spaced from recess 302 of the finger grip element 120.

Reference is now made to FIGS. 11A, 11B, 11C and 11D, which are simplified drawings of the dual chamber syringe 100 of FIGS. 1A-7C in an end of medicament reconstitution operative orientation, including respectively a simplified perspective view, a partially cut-out perspective view and two simplified sectional views taken along orthogonal lines C-C and D-D in FIG. 11B.

It is seen in FIGS. 11A-11D that the plunger rod assembly 130 is further axially forwardly advanced relative to the syringe barrel 104 by means of further thread-like rotation of the plunger rod assembly 130 relative to the finger grip element 120. The plunger rod assembly 130 is further rotated relative to the finger grip element 120 and thus relative to syringe barrel 104 about longitudinal axis 103 in the rotational direction indicated by arrow 250 and thereby longitudinally displaced forwardly along longitudinal axis 103 to provide for passage of solvent 450 into the chamber containing the drug preparation 440 through the bypass protrusion 128 of the syringe barrel 104 in order to reconstitute the drug preparation resulting in a liquid medicament solution contained between the forward piston 122 and the intermediate piston 124.

The dual chamber syringe 100 is shown at the end of medicament reconstitution in FIGS. 11A-11D, whereas the entire amount of the solvent 450 passed into the chamber containing the drug preparation 440 through the bypass protrusion 128 and created liquid medicament solution 460, now contained between the forward piston 122 and the intermediate piston 124.

It is appreciated that all spatial relationships between the various components of the dual chamber syringe 100 remain the same as described hereinabove with respect to the reconstitution operative orientation illustrated in FIGS. 10A-10D, besides the following spatial relationships:

It is a particular feature of an embodiment of the present invention that as seen particularly in FIGS. 11A-11D, in this end of medicament reconstitution operative orientation, the plunger rod assembly 130 completed its thread-like rotation relative to the finger grip element 120 and now the teeth 300 of the finger grip element 120 engage the longitudinal track portion 202 of the guiding track 200 of the plunger rod assembly 130.

It is particularly seen that upon further thread-like rotation of the plunger rod assembly 130 relative to the finger grip element 120 the teeth 300 of the finger grip element 120 reach the rearward end 222 of the helical track portion 204, then continuously pass through raised ridge 206 and snap into the longitudinal track portion 202 of the guiding track 200, having a smaller diameter than that of the raised ridge 206.

It is a further particular feature of an embodiment of the present invention that in this end of medicament reconstitution operative orientation, further rotation of the plunger rod assembly 130 relative to the finger grip element 120 is prevented, due to engagement of the teeth 300 of the finger grip element 120 with the longitudinal track portion 202 of the guiding track 200. Particularly, it is seen that teeth 300 of the finger grip element 120, are seated within the groove forming the longitudinal track portion 202 of the guiding track and are radially supported from rotating in an opposite rotational direction by engagement of teeth 300 with corresponding radially facing shoulders 210.

It is noted that the plunger rod assembly 130 is prevented from rotational displacement relative to the finger grip element 120 and relative to the syringe assembly 102 during the entire injection process due to engagement of the guided teeth 300 of the finger grip element 120 with the longitudinal track portions 202 of the plunger rod assembly 130 along the entire longitudinal extent of the longitudinal track portions 202.

It is seen that in this end of medicament reconstitution operative orientation shown in FIGS. 11A-11D, the plunger rod assembly 130 completed its entire thread-like rotational displacement for complete medicament reconstitution. It is specifically seen that the teeth 300 of the finger grip element 120 are now disposed at the forward end 224 of the longitudinal track portion 202 of the guiding track 200.

It is a particular feature of an embodiment of the present invention that teeth 300 of the finger grip element 120 are continuously guided along the helical track portion 204 and then into the longitudinal track portion 202, while passing through raised ridge 206 disposed at the rearward end 222 of the helical track portion 204.

It is seen in FIGS. 11B and 11C that the rearward piston 126 now abuts the intermediate piston 124, which has now at least partially forwardly spaced from the bypass protrusion 128 and the liquid medicament solution 460 is contained between the intermediate piston 124 and the forward piston 122.

It is appreciated that the dual-chamber syringe 100 is now ready for injection of the liquid medicament solution 460 upon removal of the outer cap element 114, subsequent removal of the inner cap element 112 and connection of a needle onto the male luer 326 of the luer lock element 110.

It is noted that the forward piston 122 is used for sealing the liquid medicament solution 460 between the two pistons 122 and 124 up to the point where the forward piston 122 reaches the intermediate portion 322 of the luer lock element 110, whereas fluid flow passage between the liquid medicament solution 460 and the male luer 326 is established through grooves 360 formed in the luer lock element 110 and thus enables injection into the injection site.

It is thus appreciated that upon axial forward displacement of the plunger rod assembly 130 relative to the syringe barrel 104, all pistons 122, 124 and 126 are displaced together up until the point where the forward piston 122 reaches the intermediate portion 322 of the luer lock element 110 and then the rearward piston 126 along with the intermediate piston 124 are displaced forwardly relative to the forward piston 122 until all liquid medicament solution 460 is transferred into the male luer 326 through grooves 360 of the luer lock element 110.

It is noted that in this end of medicament reconstitution operative orientation, the at least one protrusion 252 of the plunger rod outer portion 134 is aligned with the recess 302 of the finger grip element 120, thus providing a visual indication to the user of plunger rod threading displacement completion and thus indicates that axial displacement of the plunger rod 130 may now be initiated.

It is appreciated that alternatively any other means providing such visual indication may be used in accordance with another embodiment of the present invention. Alternatively, an audible or tactile indication of plunger rod threading displacement completion may be provided in accordance with still another embodiment of the present invention.

Reference is now made to FIGS. 12A, 12B, 12C and 12D, which are simplified drawings of the dual chamber syringe 100 of FIGS. 1A-7C in an end of injection operative orientation, including respectively a simplified perspective view, a partially cut-out perspective view and two simplified sectional views taken along orthogonal lines C-C and D-D in FIG. 12B.

It is seen in FIGS. 12A-12D that the plunger rod assembly 130 is axially forwardly displaced relative to the syringe barrel 104 by means of pushing the plunger rod assembly 130 axially along longitudinal axis 103 relative to the finger grip element 120 and thus relative to the syringe barrel 104 to provide for passage of liquid medicament solution 460 through the needle, which is now attached to the male luer 326 of the luer lock element 110.

The dual chamber syringe 100 is shown at the end of injection in FIGS. 12A-12D, whereas the entire amount of the liquid medicament solution 460 passed into the needle.

It is appreciated that all spatial relationships between the various components of the dual chamber syringe 100 remain the same as described hereinabove with respect to the end of reconstitution operative orientation illustrated in FIGS. 11A-11D, besides the following spatial relationships:

It is seen in FIGS. 12A-12D that during injection of liquid medicament solution 460, the plunger rod assembly 130 is forwardly displaced axially relative to the finger grip element 120 due to engagement of the teeth 300 of the finger grip element 120 with the longitudinal track portion 202 of the guiding track 200. It is particularly seen in FIG. 12B that the teeth 300 of the finger grip element 120 are now disposed adjacent the rearward end 226 of the longitudinal track portion 202 of the guiding track 200.

It is seen in FIGS. 12B and 12C that all three pistons 122, 124 and 126 are now disposed at their forwardmost position and abut each other, while all liquid medicament solution 460 is ejected from the dual chamber syringe 100.

Figure 13A:
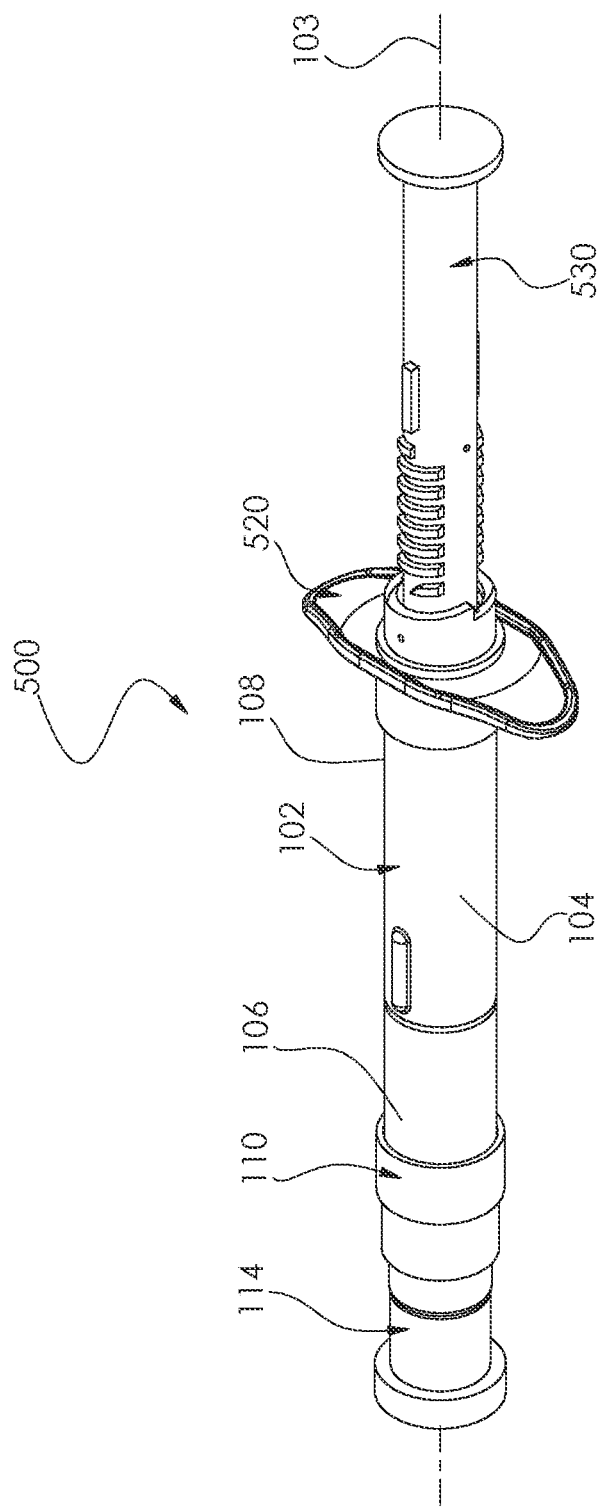
FIGS. 13A and 13B are respectively simplified pictorial view and exploded view of a dual chamber syringe constructed and operative in accordance with another embodiment of the present invention.
Figure 13B:
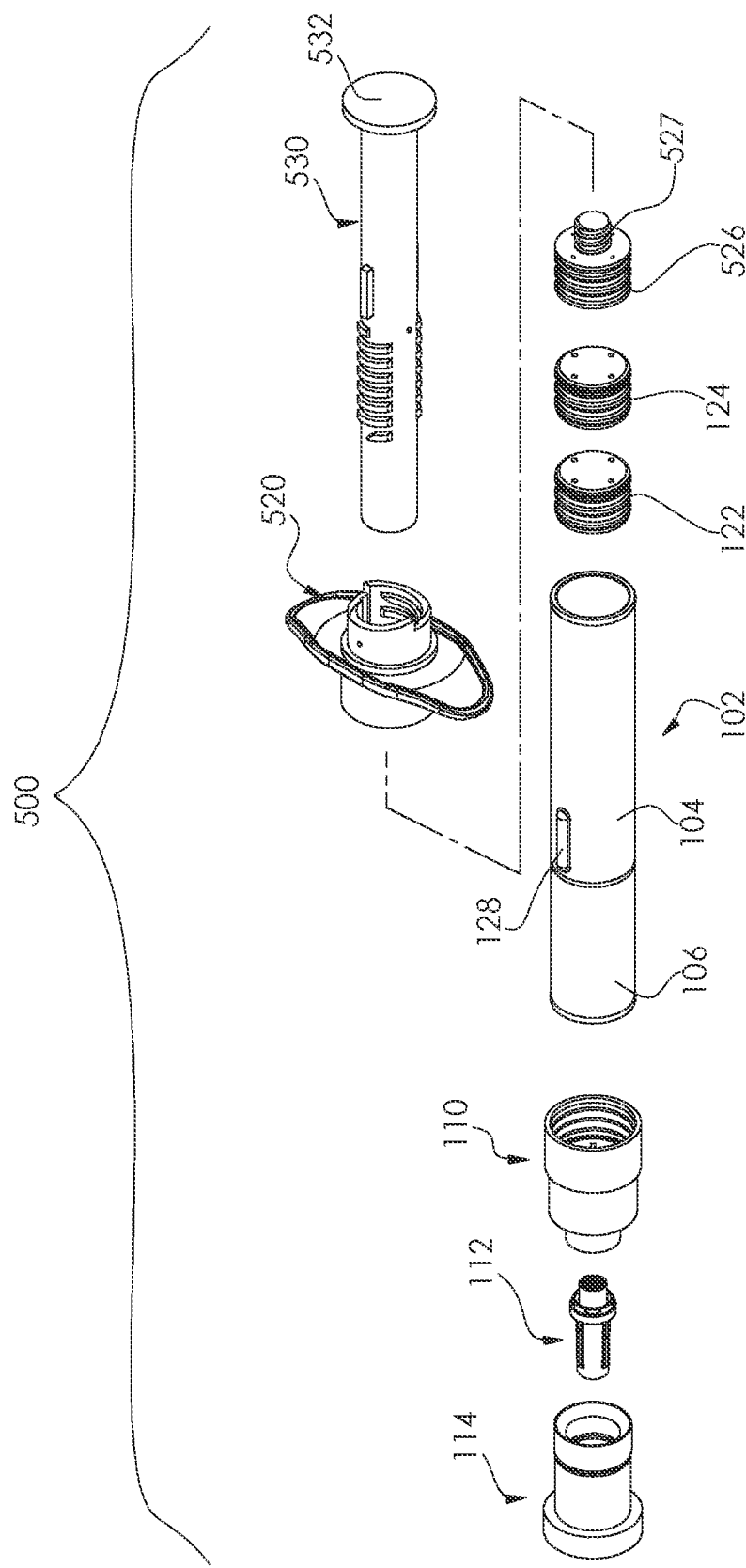

Reference is now made to FIGS. 13A and 13B, which are respectively simplified pictorial view and exploded view of a dual chamber syringe constructed and operative in accordance with another embodiment of the present invention.

A dual chamber syringe 500 constructed and operative in accordance with another embodiment of the present invention is described and illustrated in FIGS. 13A and 13B. Some of the elements of the dual chamber syringe 500 are similar or identical to the elements of dual chamber syringe 100, which is described with reference to FIGS. 1A-7C. Same elements are designated with same reference numerals.

As seen in FIGS. 13A & 13B, a dual chamber syringe 500 preferably includes syringe assembly 102 arranged along longitudinal axis 103. The syringe assembly 102 has a syringe barrel 104 having forward end 106 and rearward end 108. Luer lock element 110 is preferably fixedly and sealingly connected to the proximal end 106 of the syringe barrel 104. An inner cap element 112, which is adapted to seal and protect a portion of the luer lock element 110, and an outer cap 114 are preferably removably coupled to a forward end of the luer lock element 110.

It is also seen in FIGS. 13A & 13B that a finger grip 520 is fixedly connected to the rearward end 108 of the syringe barrel 104. The syringe assembly 102 also preferably includes three pistons, namely a forward piston 122, an intermediate piston 124 and a rearward piston 526, which are contained within the syringe barrel 104 and are adapted for slidable axial displacement relative to the syringe barrel 104. It is appreciated that a drug preparation is preferably confined between one pair of the pistons and a solvent is preferably confined between another pair of the pistons and upon appropriate longitudinal displacement of the pistons, the two substances are configured for reconstitution and subsequent ejection, as described in detail hereinbelow. It is noted that the rearward piston 526 includes an externally threaded longitudinal protrusion 127, which extends rearwardly from a rearward end of the rearward piston 526.

It is also noted that the rearward piston 526 can alternatively include a forwardly extending internally threaded socket. Further alternatively, the rearward piston 526 may include snap protrusions or recesses or any other suitable coupling means.

The syringe barrel 104 is preferably made of glass. The syringe barrel has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod 530 is operatively associated with the finger grip 520 and is displaceable with respect thereto and thus, with respect to the syringe barrel 104. In certain operative orientations. In some operative orientations, the plunger rod 530 is rotatable about longitudinal axis 103 with respect to the finger grip 520 and the syringe barrel 104. In other operative orientations, the plunger rod 530 is axially displaceable along longitudinal axis 103 relative to said finger grip 520 and the syringe barrel 104.

It is noted that outer cap 114, inner cap 112, luer lock element 110 and syringe assembly are identical in both dual chamber syringes 100 and 500. The rearward piston 526 is different from rearward piston 126 in its method of coupling with the plunger rod 530, as is described in detail hereinbelow.

Reference is now made to FIGS. 14A, 14B and 14C, which are respectively a simplified perspective view, a simplified plan side view and a simplified sectional view taken along lines C-C in FIG. 14B of the plunger rod 530 forming part of the dual chamber syringe 500 of FIGS. 13A & 13B.

The plunger rod 530 preferably is an integrally formed generally cylindrical element, preferably injection molded of plastic and is arranged along longitudinal axis of symmetry 103.

The plunger rod 530 has a longitudinal shaft 578, which preferably includes a forward end 580 and a rearward end 582 terminating at a generally circular flange 584. The circular flange 584 extends generally radially outwardly from the outer surface of the longitudinal shaft 578 and is disposed generally transversely with respect thereto. The longitudinal shaft 578 defines an outer surface 580.

Typically, two diametrically opposed generally arcshaped threaded portions 590 are formed on the outer surface 580 of the longitudinal shaft 578 and are preferably disposed in an intermediate location of the longitudinal shaft 578. It is noted that the threaded portions 590 extend generally radially outwardly from the outer surface 580. It is noted that any other number of threaded portions 590 may be formed on the outer surface 580 of the longitudinal shaft 578.

It is a particular feature of an embodiment of the present invention that a guiding track 600 is formed by the threaded portions 590. The guiding track 600 includes a helical track portion 604, which is formed as a helical groove that forms part of the externally threaded portion 590 and is defined by the track of the thread thereof.

The two threaded portions 590 are typically diametrically opposed with respect to each other. It is also noted that alternatively any number of threaded portions 590 can be arranged around the circumference of the longitudinal shaft 578 in accordance with an embodiment of the present invention.

The helical track portion 604 has a forward end 620 and a rearward end 622. The forward end 620 preferably includes a rearwardly facing tapered surface 623.

It is a further particular feature of an embodiment of the present invention that a longitudinal guiding rib 630 is formed rearwardly of the rearward end 622 of each of the helical track portion 604. The longitudinal guiding ribs 630 are preferably rearwardly spaced from rearward ends 622 of the helical track portions 604 formed by the threaded portions 590. The guiding ribs 630 extend radially outwardly from the longitudinal shaft 578 and are generally diametrically opposed to each other. The guiding ribs 630 have a rearwardly facing edge 632 and a forwardly facing edge 634, which is generally rearwardly tapered. It is noted that the rearwardly facing edge 632 of the guiding rib 630 is generally transversely arranged with respect to the longitudinal axis 103 and the forwardly facing edge 634 is disposed at an angle with respect to longitudinal axis 103. It is noted that any other number of guiding ribs 630 may be formed rearwardly of the rearward end 622 of the helical track portion 604.

The guiding rib 630 may extend longitudinally to an intermediate location along the longitudinal shaft 578. Alternatively, the guiding rib 630 may extend toward or up to abutment with flange 584 of the plunger rod 530.

It is seen in FIG. 14C that the longitudinal shaft 578 defines a forwardly facing edge 638 and an internally threaded socket 640 extend rearwardly from the forwardly facing edge 638 and adapted to be engaged with the externally threaded protrusion 527 of the rearward piston 526.

It is appreciated that alternatively the plunger rod 530 may be formed of two separate parts that are fixedly coupled to each other, similarly to the embodiment described in detail herein with reference to FIGS. 2A-3E.

It is noted that an indication for the direction of rotation of the plunger rod 530 is preferably provided on the outer surface 580 of the plunger rod 530.

It is further noted that an indication for end of plunger rod rotation is provided on the outer surface 580 of the plunger rod 530, such as at least one protrusion 642, that is preferably disposed rearwardly of rearward ends 622 of each of the helical track portions 604. It is noted that alternatively, an indication for end of plunger rod rotation can be provided by a marking placed on the outer surface 580 of the plunger rod 530.

Reference is now made to FIGS. 15A, 15B and 15C, which are respectively a simplified perspective view, a simplified plan side view and a simplified sectional view taken along lines C-C in FIG. 15B of the finger grip element 520 forming part of the dual chamber syringe 500 of FIGS. 13A & 13B.

The finger grip element 520 preferably is an integrally formed partially cylindrical hollow element, preferably injection molded of plastic and is arranged along longitudinal axis of symmetry 103.

The finger grip element 520 has a generally cylindrical base portion 670 having an outer surface 672 and an inner surface 674, defined by a through bore 676. The base portion 670 has a rearward circumferential edge 678 and a forward circumferential edge 680. Typically, two finger grip portions 682 extend generally transversely radially outwardly from base portion 670. The two finger grip portions 682 preferably extend in mutually opposite radial directions.

It is a particular feature of an embodiment of the present invention that the rearward circumferential edge 678 is comprised of two helical edge portions 690 connected to each other and forming two diametrically opposed side shoulders 692 at the connection areas of the two helical edge portions 690. Side shoulders 692 are preferably facing mutually opposite radial directions. The two helical edge portions 690 preferably have an identical slope.

The through bore 676 has a rearward bore portion 700 and a forward bore portion 702 extending forwardly therefrom. The inner diameter of the base portion 670 that is defined by rearward bore portion 700 is slightly smaller than the inner diameter of the base portion 670 defined by forward bore portion 702. Typically, several circumferential rims 704 extend radially inwardly from the inner surface 674 of the base portion 670 at the forward bore portion 702. Circumferential rims 704 are adapted for pressure-fit engagement with the syringe barrel 104.

A generally circumferential forwardly facing shoulder 706 is formed between the rearward bore portion 700 and the forward bore portion 702.

It is a particular feature of an embodiment of the present invention that typically, two mutually opposed longitudinal guiding grooves 710 are formed on the inner surface 674 of the base portion 670 at the rearward bore portion 700. Each of the guiding grooves 710 is formed adjacent the side shoulders 692. The guiding grooves 710 extend generally from the helical edge portions 690 to a location in proximity with shoulder 706.

It is a further particular feature of an embodiment of the present invention that typically two threaded portions 720 are formed on the inner surface 674 of the finger grip 520 at the rearward bore portion 700. Each of the threaded portions 720 is arranged between two guiding grooves 710. The threaded portions 720 extend radially inwardly from the inner surface 674. The threaded portions 720 define a forward end 722 and a rearward end 724, typically having a forwardly tapered edge 726 for facilitating engagement between the threaded portions 720 of the finger grip 520 and the helical track portion 604. It is noted that any other number of threaded portions 720 and guiding groves 710 may be formed on the inner surface 674 of the finger grip 520.

It is noted that at least one recess 728 is formed in base portion 670, generally slightly forwardly spaced from helical edge portion 690.

Reference is now made to FIGS. 16A, 16B, 16C and 16D, which are simplified drawings of the dual chamber syringe 500 of FIGS. 13A-15C in a storage operative orientation, including respectively a simplified partially cut-out perspective view, a simplified side plan view and two simplified sectional views taken along orthogonal lines C-C and D-D in FIG. 16B.

It is seen in FIGS. 16A-16D that the dual chamber syringe 500 is arranged along the longitudinal axis 103. The base portion 670 of the finger grip 520 is fixedly attached to the rearward end 108 of the syringe barrel 104 by means of pressure-fit engagement between rims 704 of the finger grip 520 and the outer surface of the syringe barrel 104.

The rearward portion 320 of the luer lock element 110 is fixedly attached to the forward end 106 of the syringe barrel 104 by means of pressure-fit engagement between rims 354 of the luer lock element 110 and the outer surface of the syringe barrel 104. It is seen that the intermediate portion 322 of luer lock element 110 is disposed forwardly of the forward end 106 of the syringe barrel 104, so that the longitudinal grooves 360 of the luer lock element 110 are also disposed forwardly of the forward end 106 of the syringe barrel 104. It is noted that the inner dimeter of the intermediate portion 322 is slightly larger than the inner diameter of the syringe barrel 104.

It is noted that alternatively, the syringe barrel 104 and the luer lock element 110 may be formed as an integral part. Further alternatively, a needle can be fixedly attached to the luer 326 of the luer lock element 110 or to a luer that is formed as part of the syringe barrel, in case the syringe barrel and the luer lock element are integrally formed.

The inner cap element 112 is releasably mounted over male luer 326 of the luer lock element 110 and is releasably held therein by means of engagement of undercut protrusions 336 of luer lock element 110 with protrusions 412 of the inner cap element 112. The outer cap element 114 surrounds the inner cap element 112 and is disposed in friction-fit engagement therewith. It is particularly seen that the inner cap element 112 is inserted into longitudinal bore 386 of the outer cap element 114 and the edge 384 of the outer cap element 114 is disposed adjacent or abutting with forward end 332 of the luer lock element 110.

It is additionally seen in FIG. 16D that the forward piston 122 is sealingly slidably disposed with respect to the inner surface of the syringe barrel 104 and is located generally in proximity to the forward end 106 of the syringe barrel 104. The intermediate piston 124 is also sealingly slidably disposed with respect to the inner surface of the syringe barrel 104 and is located generally between the rearward end 108 of the syringe barrel 104 and between the bypass protrusion 128.

It is noted that drug preparation 440 is confined between the forward piston 122 and the intermediate piston 124 and the forward piston 122 is used for sealing the drug preparation 440 between the two pistons 122 and 124.

It is particularly seen in FIG. 16D that the plunger rod 530 is threadably coupled to the rearward piston 526 by means of threadable interconnection between externally threaded protrusion 527 of the rearward piston 526 with internally threaded socket 640 of the plunger rod 530.

It is noted that alternatively the plunger rod 530 and the rearward piston 526 can be connected by means of threadable interconnection between externally threaded protrusion extending forwardly from the plunger rod 530 and internally threaded socket formed in the rearward piston 126. Further alternatively, the plunger rod 530 and the rearward piston 526 can be connected by means of snap coupling or any other suitable coupling means.

It is appreciated that the threading between the externally threaded protrusion 527 of the rearward piston 526 and the internally threaded socket 640 of the plunger rod 530 may have a different pitch or direction than the threading between the threaded portions 590 of the plunger rod 530 and the threaded portions 720 of the finger grip element 520. These two different threadings are configured to prevent disengagement of the plunger rod 530 from the rearward piston 526 in case the plunger rod 530 is rotated inadvertently in an opposite rotational direction than the direction indicated by arrow 250.

It is noted that solvent 450 is confined between the rearward piston 526 and the intermediate piston 124.

It is a particular feature of an embodiment of the present invention that the plunger rod 530 is operatively associated with the finger grip 520 and is displaceable with respect thereto and thus, with respect to the syringe barrel 104. In this storage operative orientation, the plunger rod 530 is partially axially inserted into the syringe barrel 104, such that the threaded portions 590 of the plunger rod 530 are not yet engaged with the threaded portions 720 of the finger grip element 520.

It is particularly seen in FIGS. 16C & 16D that the threaded portions 590 of the plunger rod 530 are axially rearwardly spaced with respect to the threaded portions 720 of the finger grip element 520. The guiding rib 630 of the plunger rod 530 is axially rearwardly spaced from the helical edge portions 690 of the finger grip element 120.

It is noted that in this storage operative orientation, the at least one protrusion 642 of the plunger rod 530 is rearwardly spaced from recess 728 of the finger grip element 520.

Reference is now made to FIGS. 17A, 17B, 17C and 17D, which are simplified drawings of the dual chamber syringe 500 of FIGS. 13A-15C in a pre-reconstitution operative orientation, including respectively a simplified partially cut-out perspective view, a simplified side plan view and two simplified sectional views taken along orthogonal lines C-C and D-D in FIG. 17B.

It is seen in FIGS. 17A-17D that the plunger rod 530 is preferably slightly axially forwardly displaced relative to the syringe barrel 104 along longitudinal axis 103 to compensate for dimension variations between the different components of the dual chamber syringe 500 and to compensate for piston displacement due to pressure variations within the syringe assembly 102, such as during shipping, for example. It is appreciated that the axial displacement of the plunger rod 530 relative to the syringe barrel 104 may be minimal in this operative orientation.

It is appreciated that all spatial relationships between the various components of the dual chamber syringe 500 remain the same as described hereinabove with respect to the storage operative orientation illustrated in FIGS. 16A-16D, besides the following spatial relationships:

It is particularly seen in FIGS. 17A-17D that in this pre-reconstitution operative orientation, the plunger rod 530 is forwardly axially displaced up to engagement of the threaded portions 590 of the plunger rod 530 with the threaded portions 720 of the finger grip element 520. Specifically, up to engagement of the tapered surfaces 623 of guiding tracks 600 of the plunger rod 530 with tapered edges 726 of threaded portions 720 of the finger grip element 520.

It is also seen in FIG. 17D that the rearward piston 526 is forwardly axially displaced relative to the syringe barrel 104 along with the plunger rod 530, due to the threadable engagement therebetween. The intermediate piston 124 and the forward piston 122 are correspondingly axially forwardly displaced relative to the syringe barrel 104 due to the hydraulic pressure created in the syringe chamber containing the solvent 450 and in the syringe chamber containing the drug preparation 440. It is noted that in this pre-reconstitution operative orientation, the intermediate piston 124 is still rearwardly spaced from the bypass protrusion 128 of the syringe barrel 104.

Figure 18C:
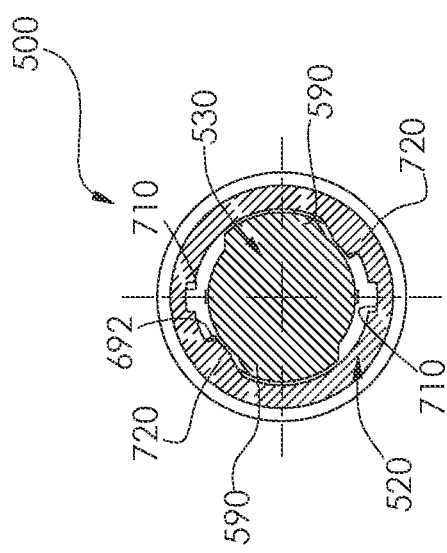

Reference is now made to FIGS. 18A, 18B, 18C and 18D, which are simplified drawings of the dual chamber syringe 500 of FIGS. 13A-15C in a medicament reconstitution operative orientation, including respectively a simplified partially cut-out perspective view, a simplified side plan view and two simplified sectional views taken along orthogonal lines C-C and D-D in FIG. 18B.

It is seen in FIGS. 18A-18D that the plunger rod 530 is axially forwardly advanced relative to the syringe barrel 104 by means of thread-like rotation of the plunger rod 530 relative to the finger grip element 520. The plunger rod 530 is rotated relative to the finger grip element 520 and thus relative to syringe barrel 104 about longitudinal axis 103 in a rotational direction and thereby longitudinally displaced forwardly along longitudinal axis 103 to provide for passage of solvent 450 into the chamber containing the drug preparation 440 through the bypass protrusion 128 of the syringe barrel 104 in order to reconstitute the drug preparation resulting in a liquid medicament solution contained between the forward piston 122 and the intermediate piston 124.

The dual chamber syringe 500 is shown during the medicament reconstitution in FIGS. 18A-18D, whereas only a portion of the solvent 450 passed into the chamber containing the drug preparation 440 through the bypass protrusion 128.

It is noted that the longitudinal dimension of the externally threaded portion 590 is preferably defined as the length that is required to axially displace the intermediate piston 124 toward the bypass protrusion 128 of the syringe barrel 104 and to axially displace the rearward piston 526 up to engagement with the intermediate piston 124.

It is appreciated that all spatial relationships between the various components of the dual chamber syringe 500 remain the same as described hereinabove with respect to the pre-reconstitution operative orientation illustrated in FIGS. 17A-17D, besides the following spatial relationships:

It is a particular feature of an embodiment of the present invention that as seen particularly in FIGS. 18A-18D, in this medicament reconstitution operative orientation, the plunger rod 530 is rotated about the longitudinal axis and due to thread-like engagement of the threaded portions 720 of the finger grip element 520 with the helical track portion 604 of the guiding track 600 of the plunger rod 530, thereby forwardly displacing the plunger rod 530 longitudinally along longitudinal axis 103.

It is noted that in this medicament reconstitution operative orientation shown in FIGS. 18A-18D, the plunger rod 530 completed only a portion of its forward longitudinal displacement required for complete medicament reconstitution. It is specifically seen that the threaded portions 720 of the finger grip element 520 are disposed at an intermediate location along the helical track portion 604 of the guiding track 600 of the plunger rod 530. The threaded portions 720 of the finger grip element 520 are now disposed between the forward end 620 and the rearward end 622 of the helical track portion 604.

Figure 18D:
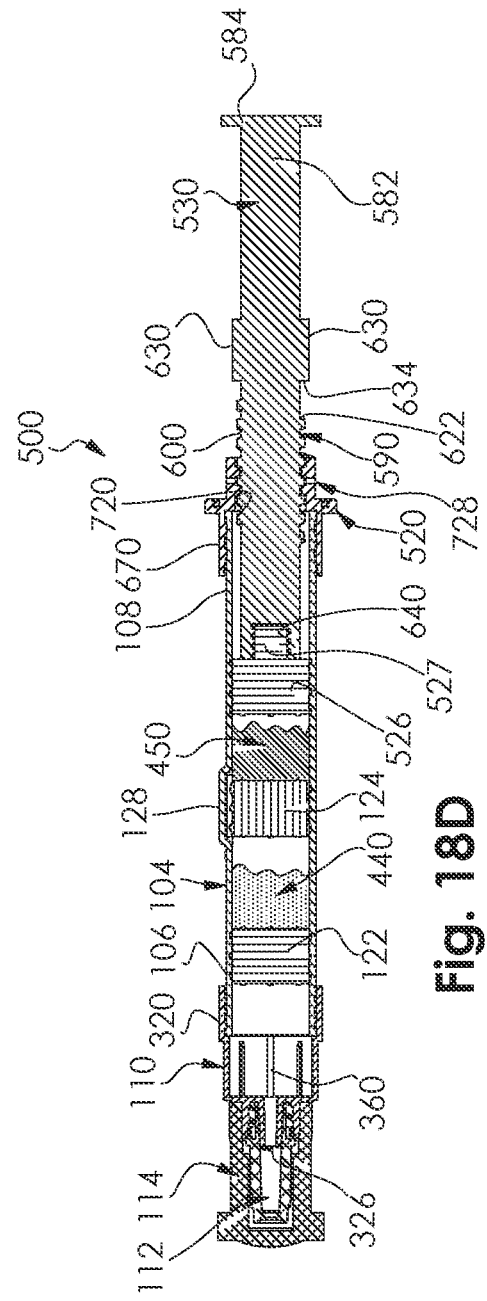

It is seen in FIG. 18D that the rearward piston 526 is forwardly axially displaced relative to the syringe barrel 104 along with the forward displacement of the plunger rod 530, due to the threadable engagement therebetween.

It is a particular feature of an embodiment of the present invention that the rotational displacement of the plunger rod 530 is translated to axial forward displacement thereof along longitudinal axis 103 due to thread-like engagement between the plunger rod 530 and the finger grip element 520, specifically between the helical track portion 604 of the plunger rod 530 and the threaded portions 720 of the finger grip element 520.

It is noted that upon initiation of axial forward displacement of the plunger rod 530, all three pistons, namely the forward piston 122, the intermediate piston 124 and the rearward piston 526 are displaced together and remain at a constant distance one from another up until the point where the intermediate piston 124 is axially aligned with the bypass protrusion 128 of the syringe barrel 104. At this point, when the intermediate piston 124 is aligned with the bypass protrusion 128, fluid flow passage is established between the two chambers of the dual chamber syringe 500 and solvent 450 is transferred into the chamber containing the drug preparation 440 through the bypass protrusion 128.

Once the intermediate piston 124 is aligned with the bypass protrusion 128, the plunger rod 530 along with the rearward piston 526 are forwardly displaced axially due to the thread-like engagement that is explained in detail hereinabove, toward the intermediate piston 124 until all solvent 450 is transferred into the chamber containing drug preparation 440.

It is noted that in this medicament reconstitution operative orientation, the at least one protrusion 642 of the plunger rod 530 remains rearwardly spaced from recess 728 of the finger grip element 520.

Reference is now made to FIGS. 19A, 19B, 19C and 19D, which are simplified drawings of the dual chamber syringe 500 of FIGS. 13A-15C prior to an end of medicament reconstitution operative orientation, including respectively a simplified partially cut-out perspective view, a simplified side plan view and two simplified sectional views taken along orthogonal lines C-C and D-D in FIG. 19B.

It is seen in FIGS. 19A-19D that the plunger rod 530 is further axially forwardly advanced relative to the syringe barrel 104 by means of further thread-like rotation of the plunger rod 530 relative to the finger grip element 520. The plunger rod 530 is further rotated relative to the finger grip element 520 and thus relative to syringe barrel 104 about longitudinal axis 103 in a rotational direction and thereby longitudinally displaced forwardly along longitudinal axis 103 to provide for passage of solvent 450 into the chamber containing the drug preparation 440 through the bypass protrusion 128 of the syringe barrel 104 in order to reconstitute the drug preparation resulting in a liquid medicament solution contained between the forward piston 122 and the intermediate piston 124.

The dual chamber syringe 500 is shown almost at the end of medicament reconstitution in FIGS. 19A-19D, whereas almost the entire amount of the solvent 450 passed into the chamber containing the drug preparation 440 through the bypass protrusion 128 and created liquid medicament solution 460, now contained between the forward piston 122 and the intermediate piston 124.

It is appreciated that all spatial relationships between the various components of the dual chamber syringe 500 remain the same as described hereinabove with respect to the reconstitution operative orientation illustrated in FIGS. 18A-18D, besides the following spatial relationships:

It is a particular feature of an embodiment of the present invention that as seen particularly in FIGS. 19A-19D, in this prior to end of medicament reconstitution operative orientation, the plunger rod 530 almost completed its thread-like rotation relative to the finger grip element 520 and now the guiding ribs 630 of the plunger rod 530 engage the helical edge portions 690 of the finger grip element 520. Specifically, forwardly facing edges 634 of the guiding ribs 630 engage helical edge portions 690 of the finger grip element 520.

It is a particular feature of an embodiment of the present invention that the slope of the helical edge portions 690 of the finger grip element 520 is different than the slope of the threaded portions 720 of the finger grip element 520. Preferably, the slope of the helical edge portions 690 is smaller than the slope of the threaded portions 720. It is noted that the slope of the forwardly facing edge 634 of guiding rib 630 of the plunger rod 530 is preferably identical to the slope of the helical edge portions 690, thus correspondingly different from the slope of threaded portions 720.

Thus, upon engagement of the helical edge portions 690 with the guiding ribs 630 of the plunger rod 530 pressure-fit is created between the plunger rod 530 and the finger grip element 520 and a threshold torque has to be exerted onto the plunger rod 530 for rotating the plunger rod 530 further and achieving engagement of the guiding ribs 630 with the guiding grooves 710 of the finger grip element 520. In the operative orientation illustrated in FIGS. 19A-19D, the dual chamber syringe 500 is shown just prior to exertion of such threshold torque onto the plunger rod 530, thus the guiding ribs 630 are not yet engaged with the guiding grooves 710.

Figure 20C:
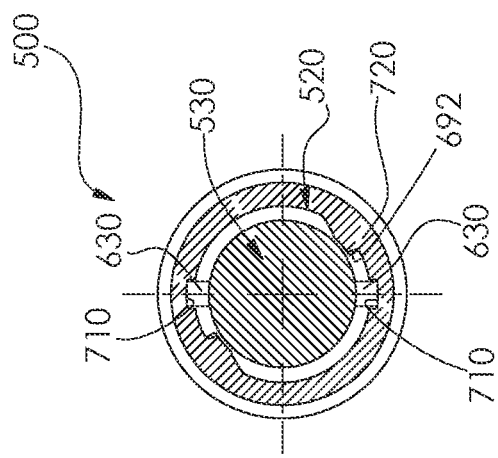

Reference is now made to FIGS. 20A, 20B, 20C and 20D, which are simplified drawings of the dual chamber syringe 500 of FIGS. 13A-15C in an end of reconstitution operative orientation, including respectively a simplified partially cut-out perspective view, a simplified side plan view and two simplified sectional views taken along orthogonal lines C-C and D-D in FIG. 20B.

It is seen in FIGS. 20A-20D that the plunger rod 530 is further axially forwardly advanced relative to the syringe barrel 104 by means of further thread-like rotation of the plunger rod 530 relative to the finger grip element 520. The plunger rod 530 is further rotated relative to the finger grip element 520 and thus relative to syringe barrel 104 about longitudinal axis 103 in a rotational direction and thereby longitudinally displaced forwardly along longitudinal axis 103 to provide for passage of solvent 450 into the chamber containing the drug preparation 440 through the bypass protrusion 128 of the syringe barrel 104 in order to reconstitute the drug preparation resulting in a liquid medicament solution contained between the forward piston 122 and the intermediate piston 124.

The dual chamber syringe 500 is shown at the end of reconstitution in FIGS. 20A-20D, whereas the entire amount of the solvent 450 passed into the chamber containing the drug preparation 440 through the bypass protrusion 128 and created liquid medicament solution 460, now contained between the forward piston 122 and the intermediate piston 124.

It is appreciated that all spatial relationships between the various components of the dual chamber syringe 500 remain the same as described hereinabove with respect to the prior to end of reconstitution operative orientation illustrated in FIGS. 19A-19D, besides the following spatial relationships:

It is a further particular feature of an embodiment of the present invention that in this end of medicament reconstitution operative orientation, further rotation of the plunger rod 530 relative to the finger grip element 520 is prevented, due to engagement of the guiding ribs 630 of the plunger rod 530 within the guiding grooves 710 of the finger grip element 520. Particularly, it is seen that when guiding ribs 630 are seated within the guiding grooves 710, radial rotation of the plunger rod 530 is prevented.

It is noted that the plunger rod 530 is preferably prevented from rotational displacement relative to the finger grip element 520 and relative to the syringe assembly 102 during the entire injection process due to engagement of guiding ribs 630 of the plunger rod 530 with the guiding grooves 710 of the finger grip element 520.

It is seen that in this end of medicament reconstitution operative orientation shown in FIGS. 20A-20D, the plunger rod 530 completed its entire thread-like rotational displacement for complete medicament reconstitution. It is specifically seen that the guiding ribs 630 of the plunger rod 530 are now disposed within the guiding grooves 710 of the finger grip element 520.

Figure 20D:
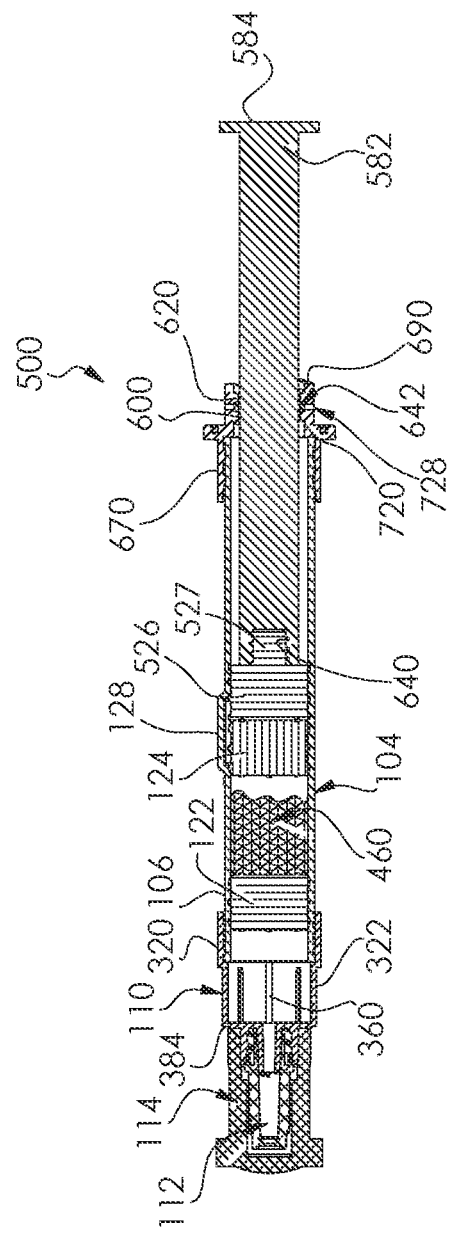

It is seen in FIG. 20D that the rearward piston 526 now abuts the intermediate piston 124, which has now at least partially forwardly spaced from the bypass protrusion 128 and the liquid medicament solution 460 is contained between the intermediate piston 124 and the forward piston 122.

It is appreciated that the dual-chamber syringe 500 is now ready for injection of the liquid medicament solution 460 upon removal of the outer cap element 114, subsequent removal of the inner cap element 112 and connection of a needle onto the male luer 326 of the luer lock element 110.

It is noted that the forward piston 122 is used for sealing the liquid medicament solution 460 between the two pistons 122 and 124 up to the point where the forward piston 122 reaches the intermediate portion 322 of the luer lock element 110, whereas fluid flow passage between the liquid medicament solution 460 and the male luer 326 is established through grooves 360 formed in the luer lock element 110 and thus enables injection into the injection site.

It is thus appreciated that upon axial forward displacement of the plunger rod 530 relative to the syringe barrel 104, all pistons 122, 124 and 526 are displaced together up until the point where the forward piston 122 reaches the intermediate portion 322 of the luer lock element 110 and then the rearward piston 526 along with the intermediate piston 124 are displaced forwardly relative to the forward piston 122 until all liquid medicament solution 460 is transferred into the male luer 326 through grooves 360 of the luer lock element 110.

It is noted that in this end of medicament reconstitution operative orientation, the at least one protrusion 642 of the plunger rod 530 is aligned with the recess 728 of the finger grip element 520, thus providing a visual indication to the user of plunger rod threading displacement completion and thus indicates that axial displacement of the plunger rod 530 may now be initiated.

It is appreciated that alternatively any other means providing such visual indication may be used in accordance with another embodiment of the present invention. Alternatively, an audible or tactile indication of plunger rod threading displacement completion may be provided in accordance with still another embodiment of the present invention.

Reference is now made to FIGS. 21A, 21B, 21C and 21D, which are simplified drawings of the dual chamber syringe 500 of FIGS. 13A-15C in an end of injection operative orientation, including respectively a simplified partially cutout perspective view, a simplified side plan view and two simplified sectional views taken along orthogonal lines C-C and D-D in FIG. 20B.

It is seen in FIGS. 12A-12D that the plunger rod assembly 130 is axially forwardly displaced relative to the syringe barrel 104 by means of pushing the plunger rod assembly 130 axially along longitudinal axis 103 relative to the finger grip element 120 and thus relative to the syringe barrel 104 to provide for passage of liquid medicament solution 460 through the needle, which is now attached to the male luer 326 of the luer lock element 110.

The dual chamber syringe 500 is shown at the end of injection in FIGS. 21A-21D, whereas the entire amount of the liquid medicament solution 460 passed into the needle.

It is appreciated that all spatial relationships between the various components of the dual chamber syringe 500 remain the same as described hereinabove with respect to the end of reconstitution operative orientation illustrated in FIGS. 20A—besides the following spatial relationships:

It is seen in FIGS. 21A-21D that during injection of liquid medicament solution 460, the plunger rod 530 is forwardly displaced axially relative to the finger grip element 520 due to engagement of the guiding ribs 630 of the plunger rod 530 with the guiding grooves 710 of the finger grip element 520.

Figure 21C:
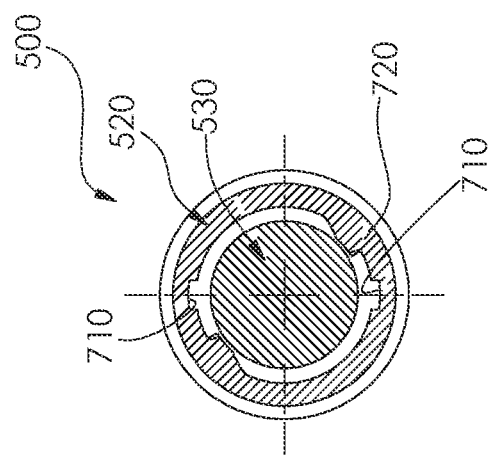
Figure 21D:
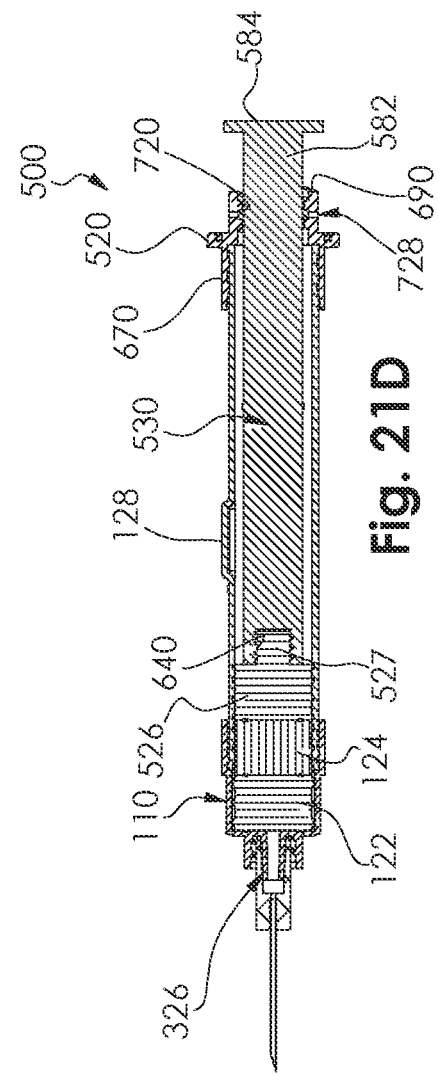

It is seen in FIG. 21D that all three pistons 122, 124 and 526 are now disposed at their forwardmost position and abut each other, while all liquid medicament solution 460 is ejected from the dual chamber syringe 500.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The invention claimed is:

1. A dual chamber syringe, comprising:
   a. a syringe barrel having a forward end, a rearward end and at least one bypass protrusion arranged along a longitudinal extend of said syringe barrel;
   b. a finger grip element coupled to said rearward end of said syringe barrel, said finger grip element comprises an inner threaded portion on an inner surface of said finger grip element and a rearward edge having at least one helical portion;
   c. a plunger rod operatively coupled with said finger grip element; said plunger rod comprises at least one threaded portion formed on an outer surface of said plunger rod and at least one guiding rib, which is rearwardly spaced from said at least one threaded portion;
   d. and wherein following relative displacement between said plunger rod and said finger grip element guided by engagement between said at least one threaded portion and said inner threaded portion, said at least one guiding rib is adapted to engage said at least one helical portion of said rearward edge.

2. The dual chamber syringe according to claim 1, and wherein at least one guiding groove is formed on an inner surface of said finger grip element, and said at least one guiding groove is radially spaced from said inner threaded portion.

3. The dual chamber syringe according to claim 2, and wherein said plunger rod is configured to be threadably displaced in a first rotational direction relative to said finger grip element upon engagement of said at least one threaded portion of said plunger rod with said inner threaded portion of said finger grip element and wherein said plunger rod is configured to be axially displaced relative to said finger grip element following engagement of said at least one guiding rib with said at least one helical portion of said rearward edge and application of sufficient force for guiding said at least one guiding rib into engagement with said at least one guiding groove.

4. The dual chamber syringe according to claim 3, and wherein rotation of said plunger rod relative to said finger grip element in a second rotational direction, opposite to the first rotational direction, is prevented due to engagement of said at least one guiding rib within said at least one guiding groove.

5. The dual chamber syringe according to claim 1, and wherein said at least one guiding rib has a tapered forwardly facing edge.

6. The dual chamber syringe according to claim 1, and also comprising a forward piston, an intermediate piston and a rearward piston slidably arranged within said syringe barrel and wherein said rearward piston is attached to said plunger rod.

7. The dual chamber syringe according to claim 6, and wherein said plunger rod is configured to be axially displaced relative to said finger grip element when at least a portion of said intermediate piston is displaced forwardly of said at least one bypass protrusion.

8. The dual chamber syringe according to claim 6, and wherein said plunger rod includes an internally threaded socket at the forward end of said plunger rod and said rearward piston includes an externally threaded protrusion extending rearwardly from said rearward piston and adapted for threadable engagement with said internally threaded socket.

9. The dual chamber syringe according to claim 8, and wherein threads of said internally threaded socket and threads of said externally threaded protrusion have a first pitch and a first direction, and threads of said inner threaded portion of said finger grip element and threads of said at least one threaded portion of said plunger rod have a second pitch and a second direction, wherein the first pitch is different than the second pitch or the first direction is different than the second direction.

10. The dual chamber syringe according to claim 1, and wherein a slope of said at least one helical edge portion is different than a slope of said inner threaded portion of said finger grip element.

11. The dual chamber syringe according to claim 10, and wherein the slope of said at least one helical edge portion is smaller than the slope of said inner threaded portion of said finger grip element.

* * * * *